United States Patent [19]
Satishchandran et al.

[11] Patent Number: 6,083,692
[45] Date of Patent: Jul. 4, 2000

[54] METHOD OF DETECTING THE PRESENCE AND MEASURING THE QUANTITY OF BIOLOGICAL POLYMERS

[75] Inventors: C. Satishchandran, Lansdale; Manoj Samuel, West Chester, both of Pa.

[73] Assignee: American Home Products Corporation, Madison, N.J.

[21] Appl. No.: 08/656,782

[22] Filed: Jun. 3, 1996

[51] Int. Cl.$^7$ .............................. C12Q 1/68; C12N 9/14; G01N 33/52; C07H 21/04

[52] U.S. Cl. ................................. 435/6; 435/196; 436/94; 536/23.1

[58] Field of Search .................................. 435/6, 196, 41, 435/91.1; 436/94, 504; 536/22.1, 23.1

[56] References Cited

FOREIGN PATENT DOCUMENTS 3053895    3/1991    Japan .

OTHER PUBLICATIONS

Doly et al. Substrate specificity and adenosine triphosphatase activity if the ATP–dependent deoxyribonulcease of *Bacillus subtilus*. Eur. J>Biochem. vol. 114:493–499, Mar. 1981.

Cerio–Ventura et al. ATP–dependent exonuclease V from *Micrococcus luteus*. The enzyme–DNA complex, the processive mechamism, and the role of ATP. BBA vol. 652:283–293, Jan. 30, 1981.

Van Dorp et al. The ATP–dependent DNAase from *Escherichia coli* rorA: A nuclease with changed enzymatic properties. BBA vol. 395:446–454, Jul. 14, 1975.

Katayama–Fujimura et al. A multiple–component, ATP–dependent protease from *Escherichai coli*. J. Biol. Chem. vol. 262:4477–4485, Apr. 5, 1987.

Fabrizio et al. Genes Dev. vol. 3:2137–2150, Oct. 1989.

Anai, M. et al., "A Deoxyribonuclease Which Requires Nucleoside Triphosphate From *Micrococcus lysodeikticus*. I. Purification and Characterization of the Deoxyribonuclease Activity", The J. of Biol. Chem. Feb. 25, 1970, 245(4), 767–774.

Anai, M. et al., "A Deoxyribonuclease Which Requires Nucleoside Triphosphate From *Micrococcus lysodeikticus*. II. Studies on the Role of Nucleoside Triphosphate", The J. Of Biol. Chem. Feb. 25, 1970, 245 (4), 775–780.

Bradford, M., "A Rapid and Sensitive Method for the Quantitation of Microgram Quantities of Protein Utilizing the Principle of Protein–Dye Binding", *Analytical Biochem.* 1976, 72, 248–254.

Burnell, J.N. and Whatley, "A New, Rapid, and Sensitive Assay for Adenosine 5'–Phosphosulphate (APS) Kinase", *Analytical Biochem.* 1976, 68, 281–288.

(List continued on next page.)

*Primary Examiner*—James Ketter
*Assistant Examiner*—William Sandals
*Attorney, Agent, or Firm*—Howson and Howson

[57] ABSTRACT

Methods of detecting the presence of linear DNA in a sample that contains circular DNA are disclosed. The methods comprise combining an ATP-dependent deoxyribonuclease, ATP and a sample to form a reaction mixture, maintaining the reaction mixture under conditions in which linear DNA is processed by the ATP-dependent deoxyribonuclease, and detecting the presence of ADP thus produced. Methods of detecting the presence of DNA, RNA, or protein in samples are disclosed. The methods comprise combining an ATP-dependent deoxyribonuclease, an ATP-dependent ribonuclease, or an ATP-dependent protease, respectively, with ATP and a sample to form a reaction mixture. The reaction mixture is maintained under conditions in which DNA, RNA or protein is processed by the respective ATP-dependent enzyme. The presence of ADP thus produced is detected, indicating the presence of the enzyme substrate. Methods of quantifying the DNA molecules, RNA molecules or protein molecules are also disclosed.

38 Claims, 8 Drawing Sheets

OTHER PUBLICATIONS

Marmur, J., "A Procedure for the Isolation of Deoxyribonucleic Acid from Micro–Organisms", *J. Mol. Biol.* 1961, 3, 208–218.

Sambrook et al., "Molecular Cloning: A Laboratory Manual", Cold Spring Harbor Press, 1989.

Satishchandran, C. and Markham, "Adenosine–5'–Phosphosulfate Kinase from *Escherichia coli* K12", The J. of Biol. Chem. Sep. 5, 1989, 264 (25), 15012–15021.

Segel, I.H., "Enzyme Kinetics", Wiley Interscience, New York, 1975.

Sterzel, W. et al., "Automated Determination of DNA Using the Fluorochrome Hoechsst 33258", *Analytical Biochem*. 1985, 147, 462–467.

Yamagishi, H. et al., "Purification of Small Polydisperse Circular DNA of Eukaryotic Cells by Use of ATP–Dependent Deoxyribonuclease", Gene 1983, 26, 317–321.

METHOD OF DETECTING THE PRESENCE AND MEASURING THE QUANTITY OF BIOLOGICAL POLYMERS

FIELD OF THE INVENTION

The present invention relates to methods of detecting the presence and amount of DNA, RNA and proteins, particularly linear DNA, linear RNA and linear proteins.

BACKGROUND OF THE INVENTION

Modern biotechnology provides new and/or improved classes of therapeutic and prophylactic agents that treat and prevent diseases, disorders, conditions and infections. Such agents can be made less expensively, more pure and more efficiently.

Protein therapeutic and prophylactic agents have been around for many years. Molecular biology offers the opportunity to find many more of such therapeutics and recombinant DNA technology has made production of proteins a relatively inexpensive undertaking. Similarly, proteins used as vaccine components can be produced in large quantities using such technology. Further, hybridoma technology allows for the production of large quantities of monoclonal antibodies.

DNA and RNA based therapeutic and prophylactic agents are becoming a growing field of product development. Advances in the understanding of biology has led to the development of several fields of endeavor, such as nucleic acid vaccines, antisense compounds and gene therapy, that use DNA- and RNA-based agents.

One problem associated with use of these types of agents is that they can be contaminated with small quantities of molecules whose presence is undesirable. For example, recombinant protein products may be contaminated with plasmid and/or chromosomal DNA. Plasmid DNA usually contains antibiotic resistance genes. The possibility of contamination of protein products by plasmid DNA therefore raises safety and public health concerns which must be addressed. Similarly, nucleic acid-based agents such as plasmid-based vaccines can be contaminated with protein or linear DNA, the administration of either as contaminants being undesirable. Antisense compounds may similarly be contaminated with proteins. The presence of contaminants in nucleic acid-based agents raises safety issues which must be addressed.

In addition to the detection of contaminants in samples of material, modern molecular biology and biochemistry methodologies often include protocols where the detection and quantitation of proteins or nucleic acids is often desirable but where current methods are impractical. For example, the concentration of purified DNA in various buffers or in water is often measured spectrophotometrically at 260 nm using the extinction coefficient of $A_{260}=1$ for a 50 $\mu$g/ml solution of double-stranded DNA or for a 40 $\mu$g/ml solution of single-stranded DNA. Purified or crude DNA samples can also be measured spectrophotometrically using various assays such as diphenylamine or by fluorescence emitted by the binding of a minor groove binding dye diamidinophenylindole. These methods require several micrograms of DNA and do not distinguish between linear and closed circular DNA. Ethidium bromide staining of agarose gels containing DNA (50–100 ng) is routinely used in a typical molecular biology lab, but estimation of the concentration of stained DNA is complicated by differences in the kinetics of dye binding to various forms of DNA. Southern and dot blot techniques are useful for qualitative analysis, but are imprecise in quantitation of the target molecule due to the large variations in the efficiencies of a multistep procedure.

Of several methods that are currently available for the detection of DNA none is more sensitive than Southern blot/dot blot which allows for detection of nanogram quantities of DNA. However, several limitations render this method useless for the precise quantitative determination of DNA concentrations. Linking the target DNA quantitatively onto a filter, the efficiency of labeling the DNA probe, salt and temperature effects, effects of neutral polymers that favor hybridization, the concentration of probe DNA during hybridization, and finally the stringent washes that remove the unhybridized and some of the hybridized probe, contribute toward the aforementioned lack of precision in Southern and dot blot methodologies designed to quantitate DNA. Current detection/quantification protocols often require samples of a size close to or greater than the size of the specimen of interest. For example, in order to find out how much DNA, RNA or protein is present in a sample, the entire sample may need to be used.

Accordingly, there is a need for methods of detecting and/or quantifying the presence and amount of nucleic acid molecules and proteins. There is a need for methods of detecting and/or quantifying the presence and amount of linear nucleic acid molecules in samples containing circular plasmids. There is a need for methods of detecting and/or quantifying the presence and amount of proteins contaminating samples containing nucleic acid molecules. There is a need for methods of detecting and/or quantifying the presence and amount of nucleic acid molecules contaminating samples containing protein molecules. There is a need for methods of measuring the amount of proteins or nucleic acid molecules present in a sample.

SUMMARY OF THE INVENTION

The present invention provides methods of detecting the presence of linear DNA in a sample that contains circular DNA. The methods comprise the steps of combining an ATP-dependent exonuclease that processes DNA, ATP and the sample to form a reaction mixture. Preferably the components used to form the reaction mixture are free of ADP. The reaction mixture is maintained under conditions in which linear DNA is processed by the ATP-dependent exonuclease for a selected amount of time sufficient for the ATP-dependent exonuclease to at least partially digest linear DNA present in the sample. The presence of ADP is then detected, either directly or indirectly. The rate at which ADP is generated by conversion of ATP to ADP associated with ATP-dependent exonuclease activity is related to the amount of linear DNA present.

In some embodiments, the ATP-dependent exonuclease is selected from the group consisting of: ATP-dependent 5' exonuclease and ATP-dependent 3' exonuclease.

In some embodiments, the ATP is gamma$^{32}$P-ATP and the presence of ADP is detected by using thin layer chromatography to separate gamma$^{32}$P-ATP, ADP and free$^{32}$ P and detecting the presence of free $^{32}$P.

In some embodiments, the ATP is alpha$^{32}$P-ATP and the presence of ADP is detected by using thin layer chromatography to separate the alpha$^{32}$P-ATP, alpha$^{32}$P-ADP and free P, and detecting the presence of alpha$^{32}$P-ADP.

In some embodiments, wherein the ATP is beta$^{32}$P-ATP and the presence of ADP is detected by using thin layer chromatography to separate the beta$^{32}$P-ATP, beta$^{32}$P-ADP and free P, and detecting the presence of beta$^{32}$P-ADP.

In some embodiments, the presence of ADP is detected indirectly by making ADP a rate limiting reactant in a reaction which can be evaluated. In some embodiments, the reaction mixture is combined with phosphoenolpyruvate (PEP), pyruvate kinase (PK), lactate dehydrogenase (LDH) and NADH or TNADH. The ADP formed when ATP is converted to ADP upon digestion of linear DNA by the nuclease becomes the rate limiting reactant for the PK-catalyzed reaction that converts PEP to pyruvate and ADP to ATP. Pyruvate then becomes the rate limiting reactant for the LDH catalyzed reaction that converts pyruvate to lactate and NADH to NAD or TNADH to TNAD. The amount of NADH or TNADH remaining is measured. If the amount of NADH or TNADH remaining is less than the amount of NADH or TNADH added to the reaction mixture, the presence of linear DNA is indicated.

In some embodiments, NADH is added to the reaction mixture, and the amount of NADH remaining is measured by spectrophotometry at 340 nm.

In some embodiments, TNADH is added to the reaction mixture, and the amount of TNADH remaining is measured by spectrophotometry at 405 nm.

The number of linear DNA molecules present in the sample can be calculated by preparing a progress curve using the reactions above with samples of known quantities of linear DNA. Progress curves are plotted with spectrophotometry data in which the velocity of reaction for known concentrations of DNA is first determined. The velocity of reaction is then plotted versus the cioncentration of DNA. The curve generated is then used to determine concentration based upon reavction velocity data generated using samples having unknown concentrations of DNA.

The present invention relates to methods of detecting the presence of DNA in a sample. The method comprises the steps of contacting a sample with an ATP-dependent nuclease, preferably in the absence of ADP. After allowing maintaining the mixture under conditions in which DNA is digested by the ATP-dependent nuclease for an amount of time sufficient for the ATP-dependent nuclease to at least partially digest DNA present in the sample, the presence of ADP generated by the ATP-dependent nuclease is then detected, either directly or indirectly. The presence of ADP generated by conversion of ATP to ADP due to ATP-dependent nuclease activity indicates the presence of DNA in the sample. The rate at which ADP is generated by conversion of ATP to ADP associated with ATP-dependent nuclease activity is related to the amount of DNA present.

The present invention relates to methods of detecting the presence of DNA in a sample. The method comprises the steps of linearizing any circular DNA that may be present in the sample by contacting the sample, and thus any circular DNA therein, with an endonuclease. After an amount of time sufficient for the endonuclease to linearize any DNA present in the sample, the sample is combined with an ATP-dependent exonuclease, ATP and said sample to form a reaction mixture. The components of the reaction mixture are preferably free of any ADP. The reaction mixture is maintained under conditions in which linear DNA is processed by the ATP-dependent exonuclease for an amount of time sufficient for the ATP-dependent exonuclease to at least partially digest linear DNA present in the sample. The presence of ADP is then detected, either directly or indirectly. The presence of ADP generated by conversion of ATP to ADP due to ATP-dependent exonuclease activity indicates the presence of DNA in the sample. The rate at which ADP is generated by conversion of ATP to ADP associated with ATP-dependent exonuclease activity is related to the amount of linear DNA present.

In some embodiments, the sample comprises components such as viral particles, protein molecules, and microorganisms.

In some embodiments, the ATP-dependent exonuclease is selected from the group consisting of: ATP-dependent 5' exonuclease and ATP-dependent 3' exonuclease.

In some embodiments, the ATP is gamma$^{32}$P-ATP and the presence of ADP is detected by using thin layer chromatography to separate gamma$^{32}$P-ATP, ADP and free $^{32}$P and detecting the presence of free $^{32}$P.

In some embodiments, the ATP is alpha$^{32}$P-ATP and the presence of ADP is detected by using thin layer chromatography to separate the alpha$^{32}$P-ATP, alpha$^{32}$P-ADP and free P, and detecting the presence of alpha$^{32}$P-ADP.

In some embodiments, wherein the ATP is beta$^{32}$P-ATP and the presence of ADP is detected by using thin layer chromatography to separate the beta$^{32}$P-ATP, beta$^{32}$P-ADP and free P, and detecting the presence of beta$^{32}$P-ADP.

In some embodiments, the presence of ADP is detected indirectly by making ADP a rate limiting reactant in a reaction which can be evaluated. In some embodiments, the reaction mixture is combined with phosphoenolpyruvate (PEP), pyruvate kinase (PK), lactate dehydrogenase (LDH) and NADH or TNAD. The ADP formed when ATP is converted to ADP upon digestion of linear DNA by the nuclease becomes the rate limiting reactant for the PK-catalyzed reaction that converts PEP to pyruvate and ADP to ATP. Pyruvate then becomes the rate limiting reactant for the LDH catalyzed reaction that converts pyruvate to lactate and NADH to NAD or TNADH to TNAD. The amount of NADH or TNADH remaining is measured. If the amount of NADH or TNADH remaining is less than the amount of NADH or TNADH added to said reaction mixture, the presence of linear DNA is indicated.

In some embodiments, NADH is added to the reaction mixture, and the amount of NADH remaining is measured by spectrophotometry at 340 nm.

In some embodiments, TNADH is added to the reaction mixture, and the amount of TNADH remaining is measured by spectrophotometry at 405 nm.

The number of linear DNA molecules present in the sample can be calculated by preparing a progress curve using the reactions above with samples of known quantities of linear DNA. The amount of NADH or TNADH remaining in the assay with the test sample can be compared to the progress curve plotted when the assay was run using known samples and the amount of linear DNA present in the test sample can be accurately determined by plotting the test data on the progress curve.

The present invention provides a method of quantifying the number of DNA molecules in a sample. According to the methods, DNA in a sample is linearized and combined, preferably in absence of ADP, with an ATP-dependent nuclease and ATP and the sample to form reaction mixtures. After maintaining the reaction mixtures under conditions in which linear DNA is processed by the ATP-dependent nuclease the presence of ADP is detected. The amount of DNA present in the sample can be calculated by measuring the amount of ATP converted to ADP in the amount of reaction time under the specific reaction conditions using the reactants used.

The present invention provides a method of quantifying the number of DNA molecules in a sample. According to the methods, a progress curve is plotted using known quantities of DNA in a reaction in which ADP is formed. In particular, various known quantities of linear DNA are combined, in separate control reactions, with an ATP-dependent nuclease and ATP to form control reaction mixtures. To plot a progress curve, the velocity of the reaction is measured initially for each of several concentrations of DNA. The velocities are then plotted versus concentration. To determine the concentration in a test sample, the velocity is determined. By plotting the velocity of the test sample, the concentration can be ascertained. The velocity of a reaction can be determined for reactions which contain less than 40 ng of DNA. In such reactions, the velocity is linear for the first 40 minutes of reaction time. Accordingly, at two or more time points within the first 40 minutes, the absorbance is measured with a spectrophotometer. The velocity is equal to slope fo the linear reaction, i.e. the change in absorbance (difference in abosorbance at different time points) over the change in time (time between time points). The velocity of reaction for different concentrations are determined and then plotted on a graph to generate a curve showing velocity and concentration. This graph is used to determine concentration from data from test reactions. Specifically, the velocity of reaction for a sample is determined. The corresponding velocity on the velocity/concentration graph is then used to quickly and accurately identify the concentration of DNA in the sample.

Using the above methodologies and an ATP-dependent nuclease that processes RNA instead of DNA, the present invention can be employed in methods of detecting RNA and quantifying RNA in samples. In methods adapted for RNA detection and quantitation that employ progress curves, such curves are generated using known quantities of RNA. This specification is intended to expressly describe each of the above DNA detection and quantification methods as adapted for RNA detection as well.

The present invention includes methods of detecting the presence of RNA by converting RNA into monomers (NMPs) using RNA degradation enzymes such as phosphodiesterase in the absence of monomeric monophosphorylated forms of at least one nucleotide and in the absence of ADP. The NMPs are then phosphorylated by an ATP-dependent NMP kinase. ADP is thus generated by the kinase reaction. The NMP is a rate limiting reactant and its generation can be detected by the detection of ADP generated by the NMP kinase reaction.

Additionally, the present invention provides methods of detecting the presence of protein molecules in a sample. The methods of detecting protein are similar to those for detecting DNA and RNA but are adapted for protein detection by employing ATP-dependent proteases and detecting the presence of ADP generated by ATP conversion due to protease activity. In the absence of ADP, an ATP-dependent protease (preferably an N- or C-terminal protease) is combined with ATP and a sample to form a reaction mixture. The reaction mixture is maintained under conditions in which protein is processed by the ATP-dependent protease for an amount of time sufficient for the ATP-dependent protease to at least partially digest protein present in the sample. The presence of ADP generated by conversion of ATP to ADP associated with ATP-dependent protease activity is detected. The ADP may be detected directly or indirectly by the same methods as described for direct and indirect ADP detection methods above for detecting DNA and RNA. This specification is intended to expressly include those methods direct and indirect ADP detection as part of methods of detecting proteins.

DETAILED DESCRIPTION OF THE INVENTION

Figure 1:
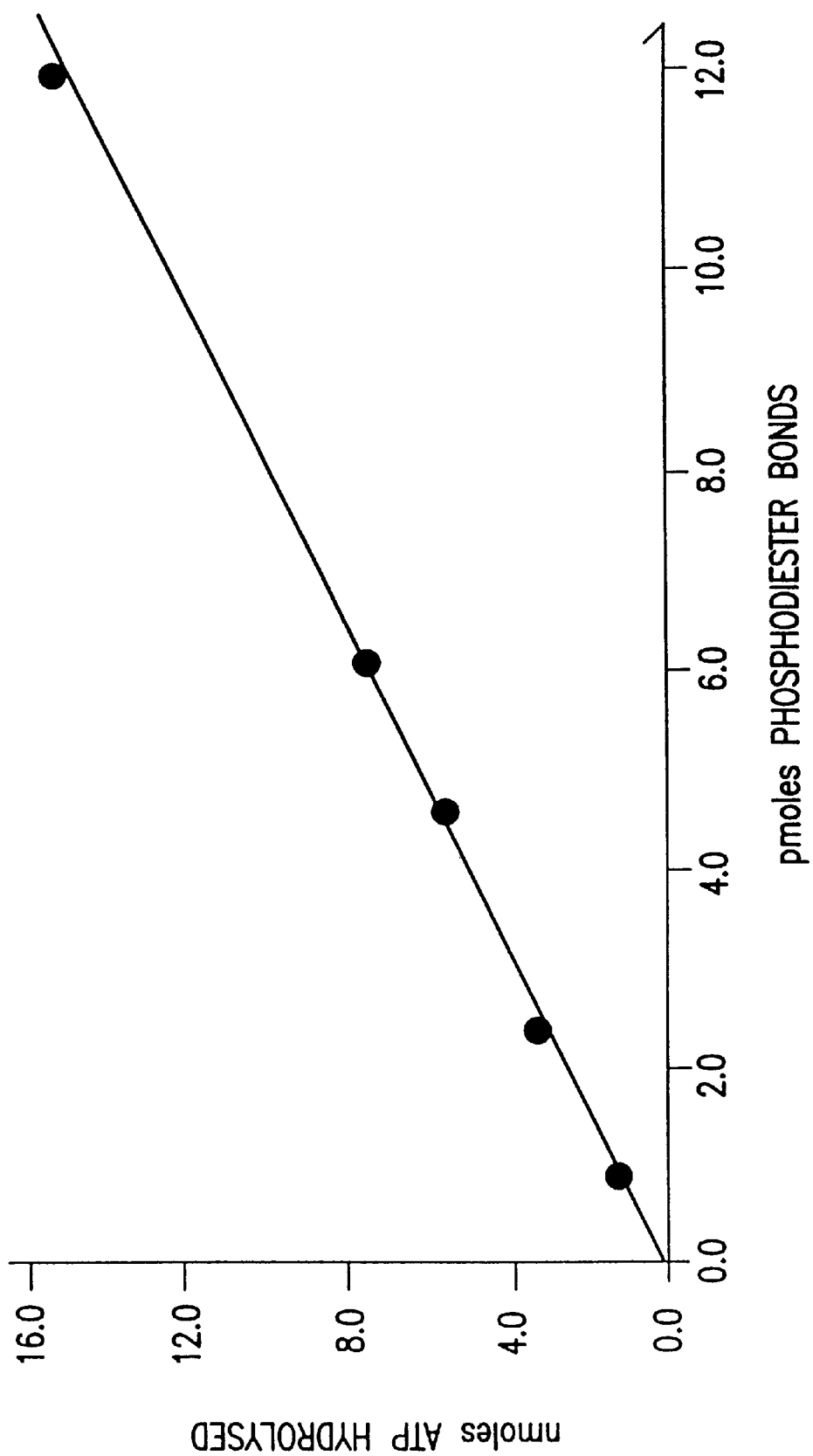
FIG. 1 shows stoichiometry of phosphodiester bond hydrolysis and of ADP formation.

As used here, the term "biological polymer" is meant to refer to proteins and nucleic acid molecules including DNA and RNA molecules.

As used herein, the term "processing" is meant to refer to any chemical reaction including enzyme mediating reactions which require energy through the conversion of ATP to ADP.

Some aspects of the present invention are useful to measure the amount of DNA present in a sample including the amount of linear DNA present in a sample that contains circular plasmid DNA. In addition, some aspects of the present invention are useful to measure the amount of RNA present in a sample. Further, some aspects of the invention are useful to measure the amount of protein in a sample including the amount of linear peptides present in a sample that contains cyclic peptides.

The present invention provides methods of detecting the presence of and measuring the amount of biological polymers present in a sample by analyzing small quantities of a sample. For example, nanogram and picogram quantities of DNA or RNA may be detected and measured which allows one to measure DNA present in samples which contain very little DNA. Nanogram quantities may be detected using methods of the invention that employ spectrophotometry. Picogram quantities may be detected using methods of the invention that employ the assay which uses radiolabeled material. Heretofore, methods required the use of the entire sample in order to detect and measure small quantities of material. Similarly, sub-nanogram quantities of protein and peptides may be detected and measured.

The ability to detect and/or measure DNA provides the means to identify the presence of DNA that contaminates pharmaceutical compositions/biologics such as vaccines, proteins and antibodies. By being able to detect and measure linear DNA in the presence of plasmid DNA, contaminating linear DNA can be detected and quantified in DNA vaccines which use plasmid DNA as an active component.

According to the invention, ATP-dependent enzymes, i.e. enzymes that use ATP as a source of energy, are employed in reactions that digest or otherwise process proteins or nucleic acids (biological oligopolymers). The ATP-dependent enzyme which specifically cleaves or otherwise processes a biological polymer is combined with the sample containing the biological polymer. When the enzyme processes the biological polymer, it uses energy in the form of converting ATP into ADP. The amount of ADP generated in such a reaction is dependent on the rate for the reaction. The rate of the reaction is dependent on, among other factors, the amount of biological polymer present. Thus, the amount of ADP generated is correlated to the amount of biological polymer present in the sample.

It is the ability to track the conversion of the energy source from ATP to ADP that provides the means to detect and measure the processing reaction and therefore the presence and quantity of the biological polymer. The generation of ADP from ATP may be measured directly or by adding reactants which is dependent on ADP and measuring the results of the reaction as an indication of ADP present and therefore biological polymer present.

The direct measurement of the generation of ADP from ATP may be achieved using radiolabelled ATP. If the radiolabelled ATP is gamma labeled, the conversion of ATP to ADP will release the radiolabelled phosphorus. Using thin layer chromatography (TLC) free, radiolabeled phosphorous can be separated from the ADP and ATP and measured, indicating the rate of the enzymatic digestion reaction which processed the biological polymer. Similarly, if the ATP is radiolabelled at the $\alpha$-P or $\beta$-P, the ADP can be separated from the ATP by TLC, the conversion of ATP to ADP can be measured and thus the rate of enzymatic activity determined. The amount of radiolabelled free P versus radiolabeled ADP on a TLC may be determined by cutting the layer and counting the amount of radiolabel present on the portion with the labeled free P and the portion with the labeled ADP using a standard scintillation counter. Likewise, the amount of radiolabelled ADP versus radiolabeled ATP on a TLC may be determined by cutting the layer and counting the amount of radiolabel present on the portion with the labeled ADP and the portion with the labeled ATP using a standard scintillation counter.

In addition to direct measurement of the conversion from ATP to ADP, the level of enzyme activity can be determined indirectly. Specifically, reactants can be provided which process ADP produced when the biological polymer is processed. In such a reaction, the ADP generated in the ATP-dependent enzyme reaction (the first reaction) becomes a reactant in a second reaction. The ADP generated in the first reaction can be measured by either measuring a product of the second reaction or measuring how much of another reactant that is expended in the second reaction is present after the second reaction. The ADP generated in the first reaction can be measured by measuring either a product of the third reaction which uses a product of the second reaction or the conversion of an energy source used in a third reaction which uses a product of the second reaction.

The generation of a product of a downstream reaction or the use of an energy source in a downstream reaction can be measured and that measurement can be used to determine the rate of ATP-dependent enzymatic activity determined. The rate of ATP-dependent enzyme activity is specific for the amount of biological polymer present.

An example of measuring ADP generated in the first reaction by measuring the conversion of an energy source used in a third reaction which uses a product of the second reaction is as follows. ADP that is produced when ATP is converted to ADP upon digestion of a biological polymer with an ATP-dependent enzyme can be reacted in a second reaction. The second reaction uses the ADP and Phosphoenolpyruvate (PEP). In the presence of a pyruvate kinase (PK), the ADP and PEP produce products of this second reaction, ATP and pyruvate. Thus, the amount of pyruvate produced is a function of the amount of ADP produced by digestion of a biological polymer with an ATP-dependent enzyme. The amount of pyruvate (a product of the second reaction) produced can be measured by, for example, measuring Nicotinamide Adenine dinucleotide (NAD) generated from Nicotinamide Adenine dinucleotide reduced (NADH) when the pyruvate is converted to lactate by (lactate dehydrogenase) LDH or by measuring the amount of NADH present after NADH is converted to NAD when the pyruvate is converted to lactate by LDH. Similarly, amount of pyruvate produced can be measured by measuring Thionicotinamide Adenine dinucleotide (TNAD) generated from Thionicotinamide Adenine dinucleotide reduced (TNADH) when the pyruvate is converted to lactate by LDH or by measuring the amount of TNADH present after TNADH is converted to TNAD when the pyruvate is converted to lactate by LDH. The amount of NADH present in a sample can be measured by measuring UV absorbance at 340 nm. The amount of TNADH present in a sample can be measured by measuring UV absorbance at 405 nm. Such reactions can be performed and measurements taken using small volumes such as the well of a 96 well plate.

In preferred embodiments, rather than determining the amount of ADP formed (energy utilized) in the reaction at a said point in time, a progress curve can be obtained by sampling the reaction at various times, such as on a microtiter plate reader. The program curves are the true rate profiles. The rate profiles allow determination of the true initial velocity rates at different substrate concentrations. The initial velocity rates are proportional to substrate concentrations when the substrate concentration is lesser than the Km value (Km is the substrate concentration at half the maximal velocity), as given by the Michaelis-Menten equation. This kinetic information can be used to plot a standard curve of velocity against concentration of substrate (linear DNA). These progress curves are used to determine the quantity of biological polymer in a sample. Alternatively, data can be generated and directly analyzed to determine the quantity of material present. However, comparison of data to progress curves generated using known quantities of starting materials provides an easier and more preferred method of calculating quantities of material present in a sample.

To plot a progress curve, the velocity of the reaction is measured initially for each of several concentrations of DNA. The velocities are then plotted versus concentration. To determine the concentration in a test sample, the velocity is determined. By plotting the velocity of the test sample, the concentration can be ascertained. The velocity of a reaction can be determined for reactions which contain less than 40 ng of DNA. In such reactions, the velocity is linear for the first 40 minutes of reaction time. Accordingly, at two or more time points within the first 40 minutes, the absorbance is measured with a spectrophotometer. The velocity is equal to slope fo the linear reaction, i.e. the change in absorbance (difference in abosorbance at different time points) over the change in time (time between time points). The velocity of reaction for different concentrations are determined and then plotted on a graph to generate a curve showing velocity and concentration. This graph is used to determine concentration from data from test reactions. Specifically, the velocity of reaction for a sample is determined. The corresponding velocity on the velocity/concentration graph is then used to quickly and accurately identify the concentration of DNA in the sample.

The invention relies upon the use of ATP-dependent enzymes which process biological polymers at the junctions which connect monomers into polymeric forms. The invention relies upon the use of an energy utilizing DNA, RNA, protein and other biological polymers, that include ATP utilizing deoxyribonucleases, such as recBC, sbc gene products or ribonucleases that use ATP, or proteases that use ATP, such as clp protease, ubiquitin, or even proteosomes, or other biological polymer degrading enzymes that utilize ATP. The invention can be extended to the use of determining supercoil density in plasmids isolated from bacteria by the use of DNA gyrase or topoisomerases that use ATP to unwind DNA and relax it. The invention can also be extended to convert a biological polymer to a product than can then be acted upon by another enzyme that utilizes ATP. An example of this is to digest RNA to completion to its monomeric unit, nucleoside monophosphate (5' NMP). The NMP can then be converted to its di- and triphosphate form, just as the metabolic pathways in the cell would do it. This is accomplished by converting nucleoside monophosphate (NMP) to its diphospho form (NDP) by either using nucleoside monophosphokinese or by converting only the monophospho form of adenise (AMP) to ADP. ATP utilized in this process can be detected either by coupling the reaction to achieve oxidation of NADH (TNADH), or by using radioactive ATP and monitoring the formation of radiolabelled ADP. For example, see Formula I. Sensitivity of detection can be furthered by catalyzing the conversion of the diphosphates (5'NDP) to its triphospho forms (5'NTP) by using NDP kinase, which uses ATP for energy. See Formula II. Therefore, in summary, we can apply the biological processes that metabolize biopolymers to its monomeric units and resynthesize the activated form of the monomeric unit and eventually the biopolymer to determine quantities of the biopolymer in a sample. See Formula III. Utilization of ATP in such a pathway when monitored is proportional to the amount of biopolymer present in the sample.

An example of this specific invention using ATP: deoxyribonuclease is of conjugating the enzyme to an antibody to use in a detection system such as ELISA, just as it is used with horseradish peroxidase (HRP) conjugated antibodies. By providing substrates and/or coupling enzymes, the amount of antibody bound can be quantitated by determining the amount of ADP and/or phosphate formed in the reaction, or by determining the oxidation of NADH (TNADH) using the coupling enzymes.

Each of the enzymes have two features in common: they process a biological polymer at a polymeric linkage and they use ATP to do so. In the case of enzymes that process DNA and RNA, the polymeric linkage of such biological polymers are the phosphodiester bond. In the case of protein and peptides, the polymeric linkage is the peptide bond. In both cases, the number of such bonds correlates to the number of monomers and the number of monomers. Moreover, in the case of exo-nucleases and enzymes the cut peptides form the terminal residues, the number of such monomers present is directly linked to the number of molecules present. Thus, the number of molecules present can be calculated using such enzymes. The use of ATP by the enzymes when processing the biological polymers allows for the detection and measurement of the presence and amount of such biological polymers, even when present in very small amounts.

According to one embodiment of the invention, a highly sensitive approach for the precise quantitative determination of linear DNA content is provided. This method has been used to determine the concentration of linear DNA in plasmid samples, PCR samples following separation of unreacted oligonucleotides, restriction enzymes digested samples, and in agarose-isolated linear DNA fragments. The assay utilizes the content of phosphodiester linkages in a polynucleotide affording an unprecedented precision and sensitivity in the determination of linear DNA even in the presence of large quantities of plasmid DNA and/or RNA. This facile method for precise quantification of linear DNA content uses an ATP-dependent deoxyribonuclease and may be used to estimate the linear DNA content of plasmid or restriction enzyme digested plasmid DNA preparations, single stranded DNA preparations, gel isolated DNA fragments, PCR products and oligonucleotides. The spectrophotometric assay described here can be used to quantify linear DNA at amounts as low as 2 ng. A TLC method [$\lambda$-$^{32}$P] ATP to detect linear DNA content as low as 10 pg is also disclosed. These methods not only allow determination of linear DNA in research samples, but also in plasmid DNA preparations being evaluated for gene therapy or genetic vaccination.

EXAMPLE

Example 1

Summary

A spectrophotometric method for quantification of linear DNA is described. The assay measures the ADP produced following digestion of linear DNA by an ATP-dependent exodeoxyribonuclease. Cleavage of the phosphodiester bond of the DNA substrate is proportional to ADP formed in the reaction which follows typical Michaelis-Menten kinetics ($K_m$ of 20 ng/100 $\mu$L, and a $V_{max}$ of 30 $\mu$nmoles/min/mg). The enzyme requires $Mg^{++}$-ATP and $Mg^{++}$-DNA as substrates, although the results suggest a requirement for yet another metal ion which may be enzyme bound. Compared with the initial velocity using double stranded-linear DNA as the substrate, no change in initial velocity is observed when linear bacteriophage single stranded DNA is used as the substrate. Covalently closed circular (CCC) and nicked open circular DNA are not substrates for the enzyme. The rate of hydrolysis of ATP is not inhibited by 1 $\mu$g RNA or covalently closed circular (CCC) DNA. The product (ADP) formed in the reaction is coupled to NADH oxidation using pyruvate kinase and lactate dehydrogenase. NAD formed in the reaction is monitored spectrophotometrically as a loss in absorbance at 340 nm. This assay directly measures the amount of linear DNA present in preparations of supercoiled (CCC) plasmid DNA, and has direct utility for monitoring the quality of plasmid preparations for gene therapy.

Materials and Methods

Biochemicals and Reagents

Pyruvate Kinase/Lactate Dehydrogenase (PK/LDH) enzyme mix (from Rabbit muscle). Nicotinamide Adenine dinucleotide reduced (NADH), Phosphoenolpyruvate (PEP), inorganic phosphate, adenosine diphosphate (ADP) and adenosine triphosphate (ATP) were purchased from the Sigma Chemical Co., St. Louis, Mo., U.S.A. Deoxynucleosidetriphosphates Taq polymerase, Bacteriophage MS2 RNA, ribosomal RNA and transfer RNA were obtained from Boehringer Mannheim Biochemicals, Indianapolis, Ind., U.S.A. All other biochemicals were of reagent grade. The ATP-dependent exonuclease at 10 units/$\mu$L was purchased from Epicentre Technologies, Madison, Wis., U.S.A. The plasmid DNA was pUC4K was purchased from Pharmacia Biotech, Piscataway, N.J., U.S.A. Lambda DNA digested with the restriction enzyme HindIII was obtained from New England Biolabs. *Escherichia coli* DH10b was obtained from Lifetechnologies, Gaithersburg, Md., U.S.A.

Preparation of DNA

The molecular biology protocols used have been described by Sambrook et al. 1989 *Molecular Cloning: A Laboratory Manual*, Cold Spring Harbor Laboratory Press, New York, N.Y., which is incorporated herein by reference.

E. coli chromosomal DNA was isolated by the procedure of Marmur, J. 1961 *J. Mol. Biol.* 3, pp. 208–218, which is incorporated herein by reference, with an average size of ~50 Kilobase pairs. Restriction enzyme digests were performed according to those suggested by the manufacturer. PCR was performed on a Perkin Elmer 9600 PCR machine. The template in the PCR protocol was pUC4K, the oligodeoxynucleotide primers (23 oligomer) flanking the aph-(3')-1a (kanamycin resistance) gene were prepared on an Applied Biosystems DNA synthesizer. The aph-3' gene in pUC4K was amplified by 30 cycles at 94° C. for 30s, 55° C. for 30s and 72° C. for 1 min. The unreacted oligodeoxynucleotides were separated from PCR products on Quiaquick PCR purification cartridge from Qiagen Inc.

Protein Assay

Concentration of protein in the enzyme solution was determined by the method of Bradford, M. M. 1976 *Anal. Biochem.* 72, pp. 248–254, which is incorporated herein by reference.

Standard (substrate) DNA

A 1 ng/$\mu$L solution of Lambda HindIII markers, restriction enzyme digested plasmid (pUC4K) DNA, single stranded bacteriophage DNA or genomic DNA were used.

Standard curves were routinely generated by using 0, 2, 6, 10, 14 and 18 $\mu$L of 1 ng/$\mu$L substrate DNA. Eighty $\mu$l of the reaction mix was incubated with up to 20 $\mu$l of DNA and dH$_2$O (total volume of 100 $\mu$l) at 25° C. The reactions were quenched with 15 $\mu$l of 200 mM EDTA, pH 8.0/NaOH, following a 30 or 40 min incubation. The reactions were read at 340 nm.

Coupled Assay

The 10× assay buffer contained tris-acetate (pH 7.8/acetate at 25° C.); 330 mM, potassium acetate; 660 mM, magnesium acetate; 100 mM, dithiothreitol; 5 mM, Triton X-100, 0.1%. The reaction mix was prepared as follows, 10× buffer; 0.250 ml, NADH; 0.250 ml (0.64 $\mu$moles), PEP; 25.0 $\mu$l (2.4 $\mu$moles), ATP; 75.0 $\mu$l (2.5 $\mu$moles), H$_2$O; 1.305 ml, PK/LDH enzyme mix; 75.0 $\mu$l, ATP dependent DNAase; 20.0 $\mu$l (200 units).

Direct Assay

The direct assay was a thin layer chromatographic procedure. The reaction mixture contained 2.5 $\mu$l of 10× buffer, 1 $\mu$l (10 units of exonuclease), 1 $\mu$l (1 $\mu$Ci [$\lambda$-$^{32}$P] ATP—30000 Ci/mmole from New England Nuclear), 2–20 ng of linear DNA, 1 mM ATP in a total volume of 24 $\mu$l. The reactions were initiated by the addition of 1 $\mu$l (10 units) of the exonuclease. Incubation was carried out at 25° C. for 20 mins. The reactions were quenched by 2.5 $\mu$l of 200 mM EDTA/NaOH; pH 8.0. The substrates and products were separated on polyethyleneimine (PEI) TLC plates (E. Merck). The separation of nucleotides was performed according to Satishchandran, C. et al. 1989 *J. Bio. Chem.* 264, pp. 15012–15021, which is incorporated herein by reference. Dried TLC plates were exposed to PHOSPHORIMAGER™ (Molecular Dynamics) plates for one hour, and were visualized and quantified. The spot intensities of the (product) P and of (substrate) ATP were used to calculate product formed as a % of total substrate.

Data Analysis

An enzyme kinetics program ENZFITTER (Elsevier Biosoft) was used to generate a plot (A$_{340}$ versus ng DNA) of the standard. The slope was calculated following a regression analysis. A similar plot of the sample (A$_{340}$ versus $\mu$L DNA) was also prepared. The slope determined from the regression analysis was used to calculate the concentration of linear DNA in the sample.

Results and Discussion

Stoichiometry of the reaction

It was determined that the sensitivity of the newly developed assay depended upon the number of phosphodiester bonds cleaved in the polydeoxynucleotide per ATP molecule hydrolysed. The optimum sensitivity was thus obtained when the ratio of hydrolysis rates of nucleotide phosphodiester bonds to ATP was small. To assess the sensitivity and the feasibility of using the method for quantification of DNA phosphodiester bonds, the stoichiometry of the reaction was determined. One nmole of ATP was hydrolysed per pmole of phosphodiester bond hydrolysed in the DNA molecule. The results are shown in FIG. 1. The reaction was performed as described in the coupled assay in Materials and Methods in the absence of lactate dehydrogenase (LDH) and NADH, for 7 hr at 25° C., with varying amounts of Lambda HindIII digested DNA (phosphodiester linkages). At the end of incubation 200 units of LDH and 0.64 $\mu$moles of NADH were added and the incubation was continued for another 10 min. to convert pyruvate (NADH) to lactate (NAD). Reactions were initiated with known varying amounts of phosphodiester linkages in the substrate DNA molecule (1 ng DNA=3 pmoles of phosphodiester bonds). Moles of NAD produced in the coupled reaction using pyruvate kinase and lactate dehydrogenase were calculated from the change in absorbance at 340 nm (molar extinction coefficient of NADH=6.23E3). Ninety seven percent of the products were mononucleotides when the reactions when taken to completion. Although the stoichiometry of the reaction was not reported for the enzyme from *Micrococcus lysodeikticus*, the average size of the products was reported to be ~5.5 nucleotides (Anai, M. et al. 1970 *J. Biol. Chem.* 245, pp. 767–774, which is incorporated herein by reference). The enzyme used in this study is therefore expected to be five-fold more sensitive for the determination of linear DNA content than the reported *Micrococcus lysodeikticus* enzyme.

Linearity of product formation

Figure 2:
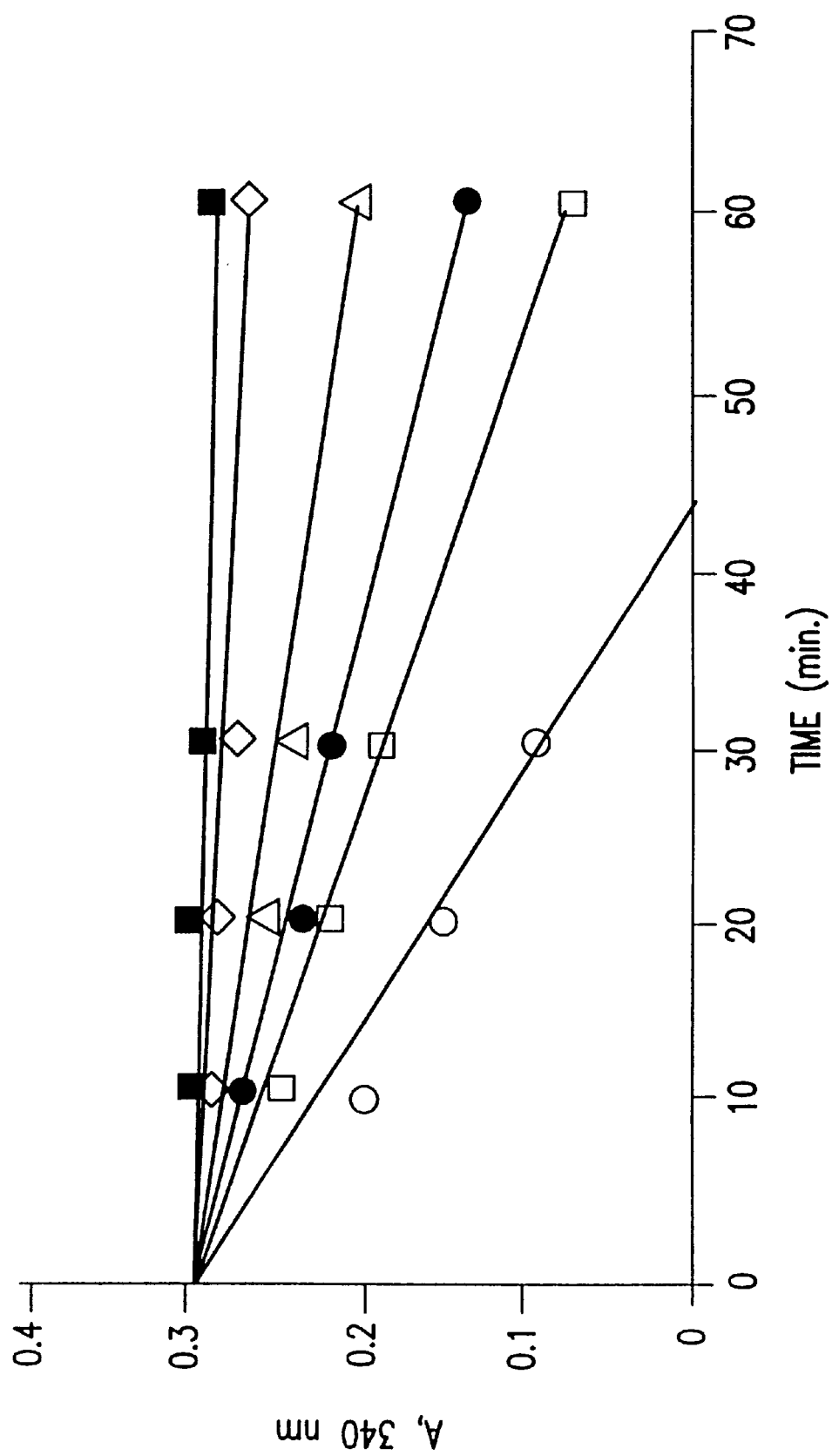
FIG. 2 shows data from Example 1 demonstrating that the enzymatic activity is linear with time.
Figure 3:
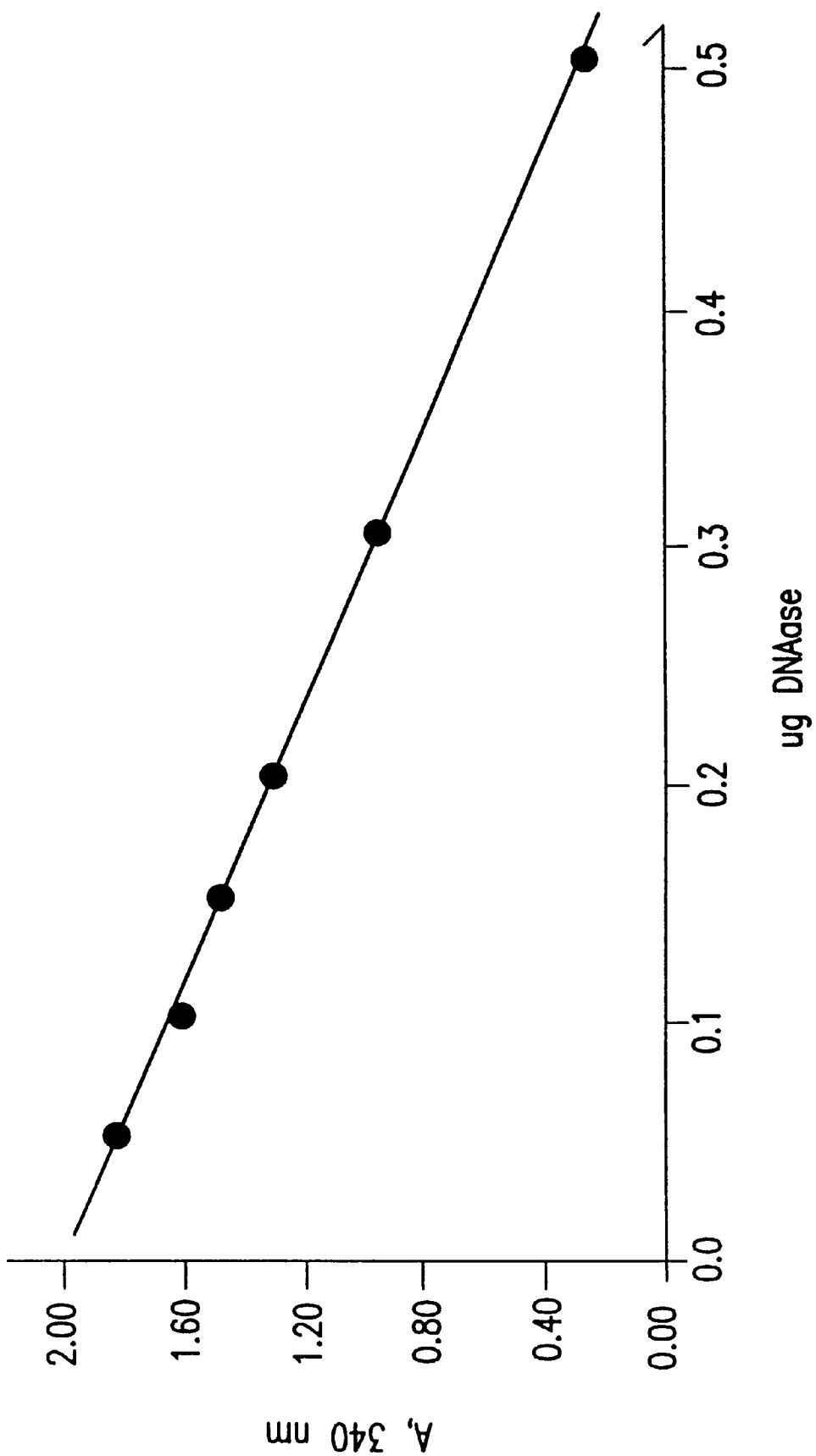
FIG. 3 shows data from Example 1 demonstrating that the enzymatic activity is linear with enzyme concentration.
Figure 4:
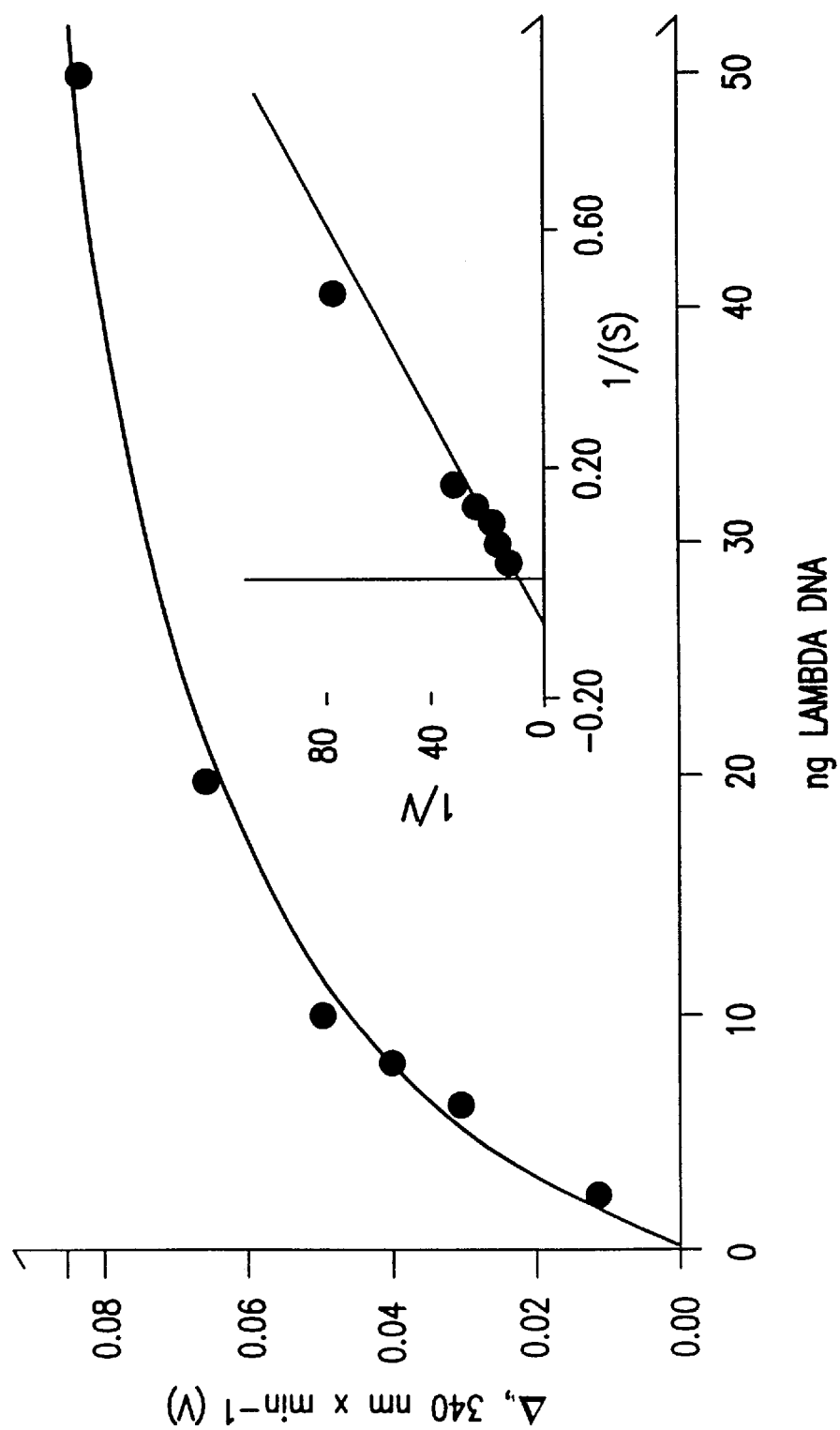
FIG. 4 shows a Michaelis-Menten plot with the inset showing a Lineweaver-Burke plot.
Figure 5A:
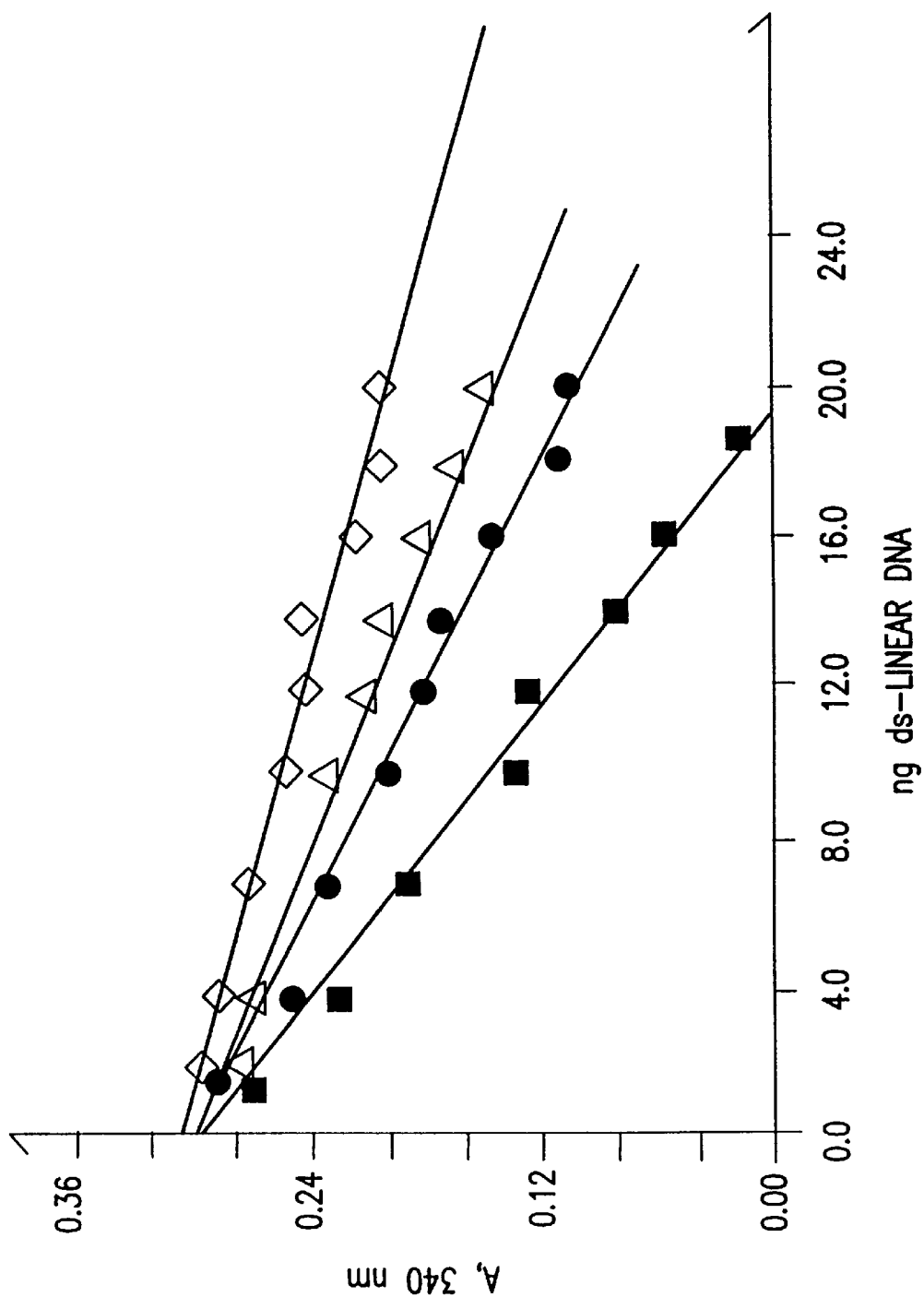
FIGS. 5A and 5B show data from Example 1 demonstrating that activity is linear with concentration of linear DNA.
Figure 5B:
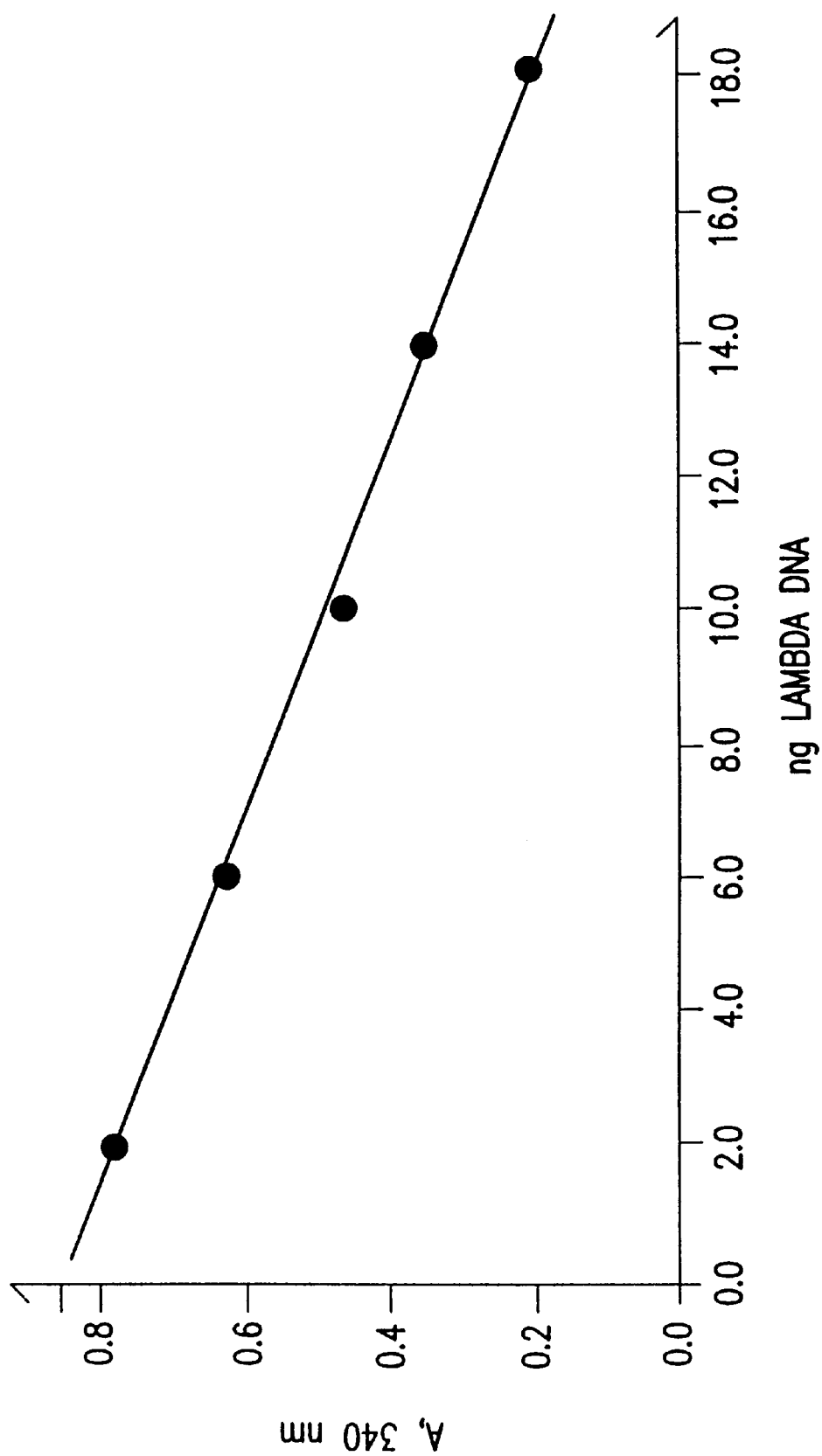

A reliable method for quantification requires that the concentration of products formed in the reaction is linear with time, concentrations of enzyme and of substrate. In the present assay, ATP hydrolysis was linear with time. The results of experiments are shown in FIG. 2. The experiments that generated the data shown in FIG. 2 are a coupled spectrophotometric assay in which the linear DNA content was varied from 2 to 20 ng. Twenty $\mu$L aliquots were removed at various times (10, 20, 30 & 60 min), and quenched by mixing with 4 $\mu$l of 200 mM EDTA as described in Materials and Methods. The samples were further diluted to 100 $\mu$l with water, to facilitate determination of optical density. ATP hydrolysis was linear with time and at least up to 40% substrate converted to products (<0.4 mM ADP and P$_i$). ADP formation was also linear with several enzyme concentrations. The results of experiments are shown in FIG. 3. The experiments that generated the data shown in FIG. 3 are a coupled assay system in which the amount of enzyme added to the reaction was varied. The enzyme was diluted using 1× reaction buffer and left on ice prior to its addition to the reaction mixture. The reaction was quenched at 15 min, with EDTA as described in Materials and Methods. ADP formation was linear with several enzyme concentrations at least until 0.36 mM ADP and P$_i$ was formed in the reaction. The reaction rates were slower when ~60% of the substrates (100 ng DNA and 1 mM ATP) were converted to products. These results suggest that product formation was inhibited either at the ATP binding site by ADP and/or P$_i$, and/or at the polynucleotide binding site by deoxynucleoside-monophosphate. The K$_m$ for DNA was 0.6 µM phosphodiester linkages (20 ng DNA/100 µL). The $V_{max}$ was 30 nmoles/min/mg enzyme. The data are shown in FIG. 4. In the experiments that generated the data in FIG. 4, the reaction was carried out in a coupled assay as described in the Methods. The reactions were initiated by the addition of enzyme. Following initiation of the 500 µl reaction; 100 µl samples were withdrawn at 1, 2, 5 and 10 min and quenched with 10 µl of 200 mM EDTA. Initial velocities were derived from the reaction rate, obtained by linear regression analysis of absorbances at 340 nm recorded at various times during the reaction. A typical Michaelis-Menten kinetic behavior exhibited by the enzyme suggests that a linear relationship must exist between velocity and concentrations of substrate below the $K_m$ value in a reaction (Segel, I. H. 1975 Enzyme kinetics, Wiley Interscience, New York, N.Y., which is incorporated herein by reference). A linear relationship between initial velocity rates and substrate concentrations was observed for all concentrations below $K_m$ for DNA. These data are shown in FIGS. 5A and 5B. The data reported in FIG. 5A is replot of FIG. 2 as a function of linear DNA content in the reaction mixture. In the experiments which generated these date, the 20 µl aliquots were quenched with EDTA as described above, at various times of incubation. FIG. 5B shows data in which the reactions were terminated at 30 min with EDTA as described in the Methods, and the absorbance at 340 nm was recorded. The results are consistent with the potential use of this enzyme to quantify linear DNA content.

Substrate specificity

Figure 6:
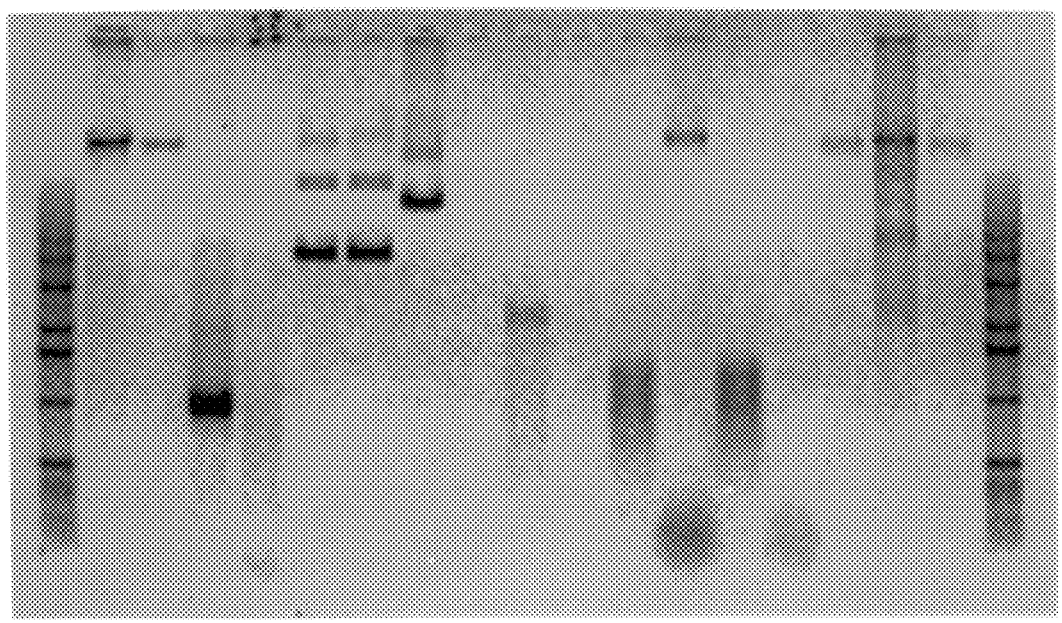
FIG. 6 shows data from Example 1 that demonstrates substrate specificity and the effect of polynucleotides and chelating agents.

Specificity of a reaction is paramount in the development of a method for quantification. It might also be anticipated that an assay to detect linear DNA would be used routinely under conditions where other potentially reactive molecules might be present, it was important to evaluate the specificity of this assay. Enzymatic activity was detected only with linear DNA molecules (linear double-stranded and linear single-stranded DNA), as reported by the manufacturer and in the literature (Anai, M. et al. 1970 J. Biol. Chem. 245, pp. 767–774, Anai, M. et al. 1970 J. Biol. Chem. 245, pp. 775–784 and Yamagishi, H. et al. 1983 Gene 26 pp. 317–321, which are each incorporated herein by reference). All linear DNA molecules and long oligonucleotides (>100-mer) had similar $K_m$ and $V_{max}$ (Table 1). No activity (as judged by agarose gel electrophoresis and ethidium bromide) was detected when nonlinear (relaxed, nicked and supercoiled) forms of DNA were used as substrates in the reaction, consistent with those reported by the manufacturer of the enzyme and those reported for similar enzymes from various sources. The date is shown in FIG. 6. FIG. 6 shows an agarose gel electrophoretogram of the reaction which was carried out for 30 min in the presence and in the absence of ATP with either 100 ng of DNA (RNA), or 100 ng each both RNA and DNA, as described in the direct assay in Methods, except that unlabeled ATP substituted the $^{32}P$ radiolabelled nucleotide in the reaction. Twenty microliters of the reaction was electrophoresed on a 1% SEAKEM (FMC Inc.) agarose gel at 60 volts for 3 hr. in TBE buffer. Lane 1 contains 1 kilo-basepair DNA markers. Lanes 2 and 3 contain E. coli chromosomal DNA with (+) and without (−) ATP, respectively. Lanes 4 and 5 contain PCR amplified DNA (+) and (−) ATP, respectively. Lanes 6 and 7 contain plasmid DNA preparation (+) and (−) ATP, respectively. Lanes 8 and 9 contain plasmid DNA digested with a restriction enzyme (+) and (−) ATP, respectively. Lanes 10 and 11 contain single-stranded M13 DNA (+) and (−) ATP, respectively. Lane 12 contains restriction enzyme digested plasmid DNA in the presence of MS2 RNA (+ATP). Lane 13 contains E. coli chromosomal DNA in the presence of MS2 RNA (+ATP). Lane 14 contains MS2 RNA (+ATP). Lane 15 contains t-RNA (+ATP). Lane 16 contains Lambda HindIII digested DNA (+ATP). Lane 17 contains Lambda HindIII digested DNA in the presence of 20 mM EDTA (+ATP). Lane 18 contains Lambda HindIII digested DNA in the presence of 50 µM citrate (+ATP). Lane 19 contains 1 kilo-basepair DNA markers. ATP hydrolytic activity of less than 0.2% of that observed for 50 ng linear DNA, was detected when circular plasmid DNA at 1 ug was used as the substrate (Table 2). No detectable enzymatic activity was observed when circular DNA molecules were used as substrates, indicating that endonucleolytic activity was minimal. MS2 bacteriophage RNA, ribosomal RNA and transfer RNA were not substrates, as judged by ethidium stain following gel electrophoresis. Moreover an ATP hydrolysis rate of less than 0.2% was observed when any of the RNAs were used as the substrate at 1 µg, as compared to the rate observed for 50 ng of linear DNA (Table 2). The substrate specificity for deoxyribose and the lack of endonucleolytic activity suggest the enzyme is a 3' exonuclease. Experiments are now underway to address the mechanistic aspects of its catalysis.

Divalent cation requirement

Neither the DNA nucleolytic activity nor the ATP hydrolytic activity were observed in the absence of a divalent cation. Therefore, divalent cation-DNA and/or divalent cation-ATP are likely to be the true substrates for the reaction. EDTA at molar equivalent to the divalent cation used in the assay quenched the enzymatic reaction (Table 3). Citrate at 1 mM inhibited the ATP hydrolytic activity (30%) even in the presence of 10 mM $Mg^{++}$ (Table 3), suggesting a requirement for another divalent cation not provided in the reaction mix, possibly of enzyme bound nature. However, citrate at 50 µM enhance the enzymatic activity by nearly 50%, possibly by chelating free divalent inhibitors of the reaction.

Potential inhibitors of the reaction

Ribonucleic acids (bacteriophage MS2 RNA) and circular plasmid DNA were not inhibitory when present in the reaction mix at 1 µg. The rate of hydrolysis, when monitored in a reaction that contained 5, 10 or 15 ng of double-stranded linear DNA was not inhibited by 200 ng RNA (t-RNA or r-RNA), or 500 ng circular DNA (Table 3). At concentrations beyond 4% ethanol the enzymatic activity was severely inhibited (Table 3). Product inhibition was caused by ADP and $P_i$, and was observed only upon >50% conversion of the substrates ATP and DNA.

Direct Assay

Figure 7:
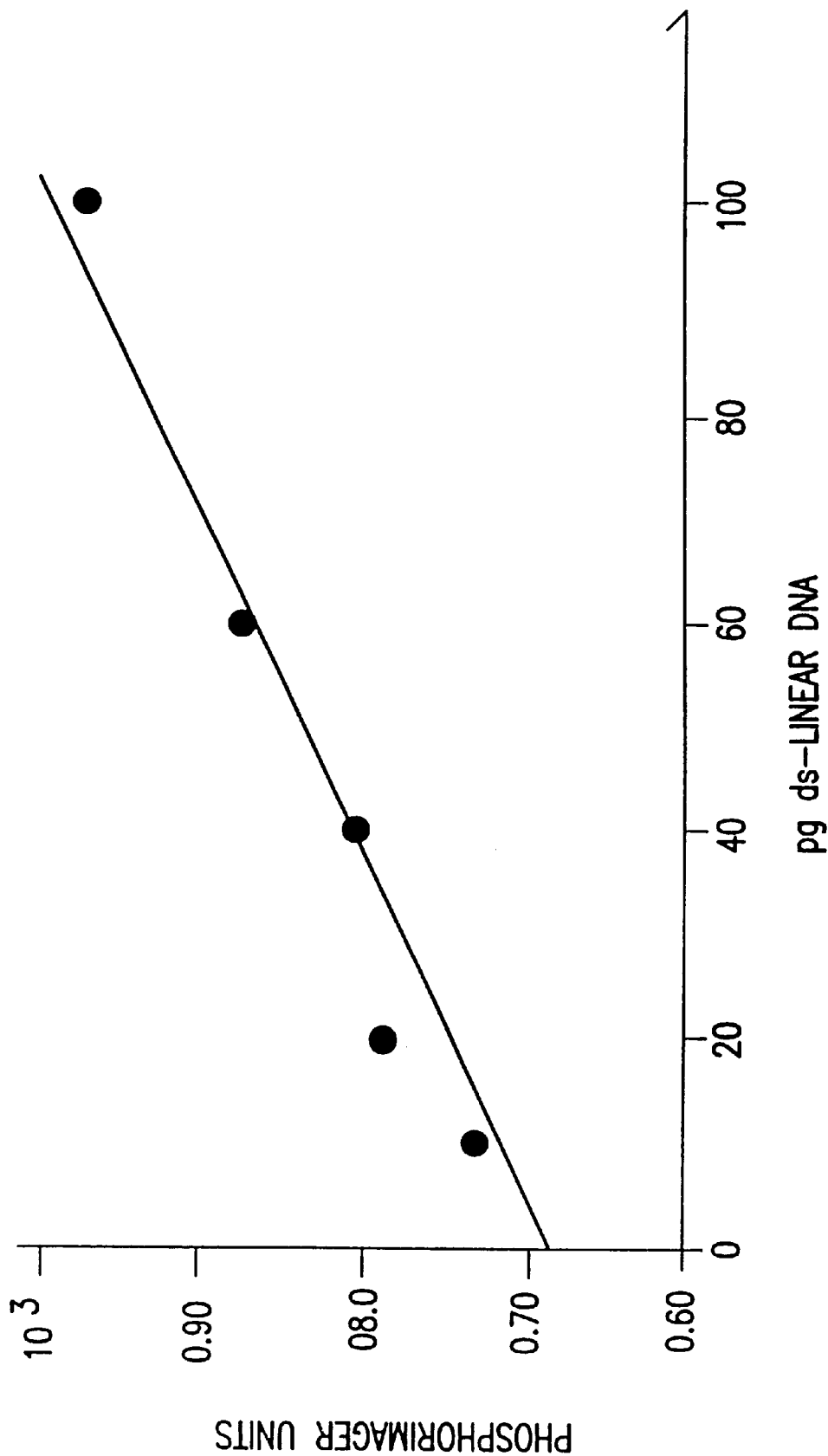
FIG. 7 shows data from Example 1 demonstrating increased sensitivity and linearity with DNA concentrations by the direct assay.

A direct assay using [$\lambda$-$^{32}P$] ATP in the reaction mix, and the quantitation of $^{32}P_i$ following TLC separation was also designed. This assay could routinely detect picogram quantities of DNA. Data demonstrating this is shown in FIG. 7. The data in FIG. 7 was generated by the assay as described in the direct assay in Materials and Methods, using an ion exchange TLC method. The TLC sheets were exposed to PHOSPHORIMAGER™ and quantitated. PHOSPHORIMAGER™ pixel units are plotted against the amount of linear double-stranded DNA varied as shown.

Example 2

Described in this report are two spectrophotometric methods in the visible spectrum to quantify DNA concentrations in an analytical laboratory. Spectrophotometric methodology has been adapted to allow processing of a large number of samples simultaneously, using a microtiter plate reader. DNA concentrations as low as 2 ng in 200 µL can be detected by this method. Using this method, a precise method of DNA concentrations have been made, of samples derived by PCR, restriction digests, chromosomal DNA isolated by several methods, and of single stranded bacteriophage DNA. The methods involve the use of either a thionicotinamide analog of NADH which absorbs at 400 nm or of DT-diaphorase to reduce nitroblue tetrazolium using NADH to form a formazan compound that absorbs at 550 nm.

Materials & Methods

Biochemicals and Reagents: Pyruvate Kinase/Lactate Dehydrogenase (PK/LDH) enzyme mix (from Rabbit muscle), Thio-nicotinamide adenine dinucleotide reduced (Thio-NADH), Phosphoenolpyruvate (PEP), inorganic phosphate, adenosine diphosphate (ADP) and adenosine triphosphate (ATP) were purchased from Sigma Chemical Co. Deoxy-nucleosidetriphosphates were obtained from Boehringer Mannheim Biochemicals. Taq polymerase was purchased from Boehringer Mannheim Biochemical. All other biochemicals were of reagent grade.

Thio-NADH: Thio-NADH stock solution was prepared at 2 mg/mL, the molar extinction coefficient of $10.3 \times 10^3$ at 400 nm was used to calculate its concentration.

Poly-deoxyribonucleotide hydrolase: The ATP-dependent exonuclease at 10 units/$\mu$L was from Epicentre Technologies, Wisconsin.

Nucleic acids: Bacteriophage MS2 RNA, ribosomal RNA and transfer RNA were of the highest quality and were obtained from Boehringer Mannheim Biochemicals. The plasmid DNA was pUC4K from Pharmacia Biotech. Lambda DNA digested with the restriction enzyme HindIII was obtained from New England Biolabs.

Cells: Escherichia coli DH 10b was from Lifetechnologies.

Preparation of DNA: All molecular biology protocols were those described by Sambrook (Supra). E. coli chromosomal DNA was isolated by the procedure of Marmur (Supra), with an average size of ~50 Kilobase pairs. Chromosomal DNA from rabbit muscle was isolated either by proteinase-K, phenol/chloroform method or by using GENECLEAN™ purifying procedure using the kit from Clontech, Inc. Due to variable effects of an enzymatic assay method by the buffer components (NaI and ethanol) in DNA isolated by the GENECLEAN™ purifying procedure, the samples often had to be preweighed, SPEEDVAC™ centrifuge (Savant, Inc.) dried and reconstituted in sterile $dH_2O$ to the appropriate pre-dry weight. This method of sample preparation appeared to remove most of the components in the DNA sample prepared by GENECLEAN™ purifying that interfered with the assay. Ethanol precipitation of DNA is recommended for further removal of assay interfering substances. Restriction enzyme digests were according to those suggested by the manufacturer. PCR was performed on a Perkin Elmer 9600 PCR machine. The template in the PCR protocol was pUC4K, the oligodeoxynucleotide primers (23 oligomer) flanking the aph-(3')-ll (kanamycin resistance) gene were prepared on an Applied Biosystems DNA synthesizer. The aph-3' gene in pUC4K was amplified by 30 cycles at 94° C. for 30s, 55° C. for 30s and 72° C. for 1 min. The unreacted oligodeoxynucleotides were separated from PCR products on Quiaquick PCR purification cartridge from Qiagen Inc.

Standard (substrate) DNA: A 1 ng/uL solution of Lambda HindIII markers, restriction enzyme digested plasmid (pUC4K) DNA, single stranded bacteriophage DNA or genomic DNA (isolated from E. coli by the method of Marmur) were used.

Standard curves were routinely generated by using 0, 4, 8, 12, 20, 29 and 36 $\mu$L of 1 ng/$\mu$L substrate DNA. One hundred and sixty microliters of the reaction mix was incubated with up to 40 $\mu$L of DNA and $dH_2O$ (total volume of 200 $\mu$L) at room temperature. The reactions were pipetted in the following order; the DNA solution (total volume, 40 $\mu$L) is added to the 96 well microtiter plates (Costar), followed by 160 $\mu$L of the reaction mix. The microtiter plate was read without much delay as described in "Data Acquisition and Analysis" section.

Sample assay: Most samples were used without any pretreatment. PCR samples were deproteinised and purified away from unreacted oligonucleotides and nucleotides. GENECLEAN™ purifying isolated DNA was pretreated as described earlier. However, all samples were diluted to achieve a concentration of 2–10 ng/5 $\mu$L, and were run in duplicate at 5 and 10 $\mu$L each. Following analysis of the raw data the concentration of DNA determined (ng/$\mu$L) for each of the two sample volumes is used to assess the presence of assay inhibitory (activating) components in the sample.

Coupled assay: The 10x assay buffer contained tris-acetate (pH 7.8/acetate at 25° C.); 330 mM, potassium acetate; 660 mM, magnesium acetate; 100 mM, dithiothreitol; 5 mM, triton X-100; 0.1%. The reaction mix is prepared as follows, 10x buffer; 0.250 ml, Thio-NADH; 0.300 ml (0.8 $\mu$moles), PEP; 25.0 $\mu$l (2.4 $\mu$moles), ATP; 75.0 $\mu$l (2.5 $\mu$moles), $H_2O$; 1.305 ml, PK/LDH enzyme mix; 75.0 $\mu$l, ATP dependent DNAase; 20.0 $\mu$l (200 units).

Data Acquisition and Analysis: The microtiter plates were read every two minutes in the kinetic mode at 405 nm for 40 min. using the VMAX™ microplate reader system of Molecular Devices, and the data were analyzed using the SOFTMAX™ software. The rate profile of each reaction is usually monitored to verify linear kinetics during the period of the assay that is used for data analysis. At the time of analysis, an O.D. limit is set to avoid non-linear part of the reaction from participating in the calculation of the initial velocity rates, and a lag time is used to avoid mixing artifacts. The rate of change in absorbance at 405 nm of the standards is used to calculate the value per nanogram (slope).

Results and Discussion

Linearity of product formation

Reliable quantitation requires that product formation (substrate utilization) is linear with time, concentrations of enzyme and substrate. DNA dependent ATP hydrolysis (Thio-NADH utilization) was linear with time (FIG. 1), as also observed using NADH.

NADH utilization was demonstrated to be linear with enzyme concentrations, and was similarly linear when Thio-NADH was used instead (FIG. 2).

Thio-NAD formation was also determined to be linear with substrate concentrations below the km value (FIG. 3), as was reported using NADH as the substrate for the reporting coupling enzyme.

The linearity of Thio-NADH oxidation with substrate concentrations up to 40 ng in 200 $\mu$L, with enzyme concentrations, and with time confers reliability and precision in the determination of DNA concentrations.

Most accurate duplicates were obtained when the assay was initiated using ATP. The 160 $\mu$l reaction mix was differently made up to contain all components except ATP in 100 $\mu$l, and appropriate amount of ATP was delivered in 60 $\mu$l. The preferable order of additions is as follows: 40 $\mu$l of DNA (DNA+$dH_2O$), 100 $\mu$l of the minus ATP reaction mixture, mixed gently and the reactions now initiated by the addition of 60 µl ATP. The above described order of addition of the assay components prevented mixing artifacts that occur in reactions at sub-$k_m$ concentrations resulting in rapid changes in substrate concentrations, and thus affecting the determination of accurate initial velocity rates.

Stoichiometry of phosphodiester cleavage to ATP hydrolysis

One of the determinants of sensitivity is stoichiometry of the reaction. A stoichiometry of less than one is less sensitive than a stoichiometry of one. Stoichiometry of ATP hydrolysed, as monitored by Thio-NADH oxidation to moles of phosphodiester bond cleaved in the polynucleotide was determined to be 1089 (FIG. 3). This makes the assay extremely sensitive as compared to assays that have a lesser stoichiometry.

Alternate substrates

Chromosomal DNA, plasmid DNA digested with a restriction enzyme, PCR generated products, single stranded linear DNA were all ideal substrates for the reaction, and their respective reaction rates were indistinguishable from each other (FIG. 4). The recovery of quantitatively (with >90% accuracy) spiked Lambda DNA digested with HindIII, from crude extracts of *E. coli* strain DH10 prepared by alkaline lysis has been made. The samples were prepared by spiking known amount of Lambda DNA to the extracts, incubated at 98° C. for 10 min. to inactivate DNAase, ATPase and NADH oxidase activities. The sample as centrifuged to rid of coagulated proteins, and were appropriately diluted to obtain initial velocity rates in the linear range of the assay. Extracts not spiked with DNA were also treated and diluted similarly, and were used as blanks.

Sensitivity and Specificity

Comparison of the reaction rates of long Lambda HindIII digested DNA and that of the *E. coli* chromosomal DNA prepared by the method of Marmur (Supra) correlated well with the concentration as determined by their absorbances at 260 nm. However, chromosomal DNA from rabbit tissues prepared by GENECLEAN™ purifying (Clontech, Inc.) gave poor UV absorption spectra (FIGS. 5A and 5B), making DNA concentration determination from absorption at 260 nm unreliable (FIG. 6). However, the concentration of DNA could be reliably determined by the enzymatic assay described here when samples were prepared as described in "Methods". An agarose gel electrophoresis of identical amounts of tissue isolated chromosomal DNA, based on its concentration as determined by the enzymatic assay is shown (FIG. 7). The concentration of DNA thus determined from rabbit tissue samples visually appear to be similar to that determined for *E. coli* DNA which had previously been shown to be in agreement with the concentration when derived from its absorbance at 260 nm.

The nearly 1.7 fold higher molar extinction coefficient of Thio-NADH allows the method to be far more sensitive than in a reaction that uses NAD. Besides, the shift in the absorption maxima to 400 nm for the Thio-NADH from that of NADH at 340 nm not only allows for visible spectrophotometry in the range of microtiter plate analysis, but also reduced the UV absorptive contribution at 340 nm, of components of a DNA prep.

Specificity of the enzyme also contributes to sensitivity of the assay, by decreasing noise due to endogenous and competing enzymic activities. The enzyme is highly specific for linear DNA, double and single-stranded. Neither was ATP hydrolysis observed above background when circular DNA was used as the substrate, nor was large concentrations of circular DNA (100 fold $K_m$ concentrations for linear DNA) inhibitory to the rate of hydrolysis of linear DNA and of ATP when at sub-$k_m$ concentrations of linear DNA. The microtiter plate format allows the assay to be performed easily and conveniently. The raw data plots a microtiter plate kinetic assay allow close inspection of the rates of Thio-NAD formation in individual samples to assure extraction of true initial velocity rates.

TABLE 1

Kinetic Constants for various substrates[a]

| Substrates | $K_m$ (µM) | $V_{max}$ (nmoles/min/mg protein) |
|---|---|---|
| Chromosomal DNA | 0.613 | 30.6 |
| PCR amplified DNA | 0.608 | 28.7 |
| HindIII digested plasmid DNA | 0.601 | 31.4 |
| Agarose-isolated linear DNA | 0.618 | 31.3 |

[a]the reactions were carried out as described in Methods, and as described in the legend to FIG. 4. The amount of DNA in the reaction was varied based on their concentrations as determined from absorbance at 260 nm, to obtain their respective initial velocity rates. The data was fitted to a Michaelis-Menten hyperbola using a computer program ENZFITTER ™ (Elsevier Biosoft) to determine the kinetic constants.

TABLE 2

Substrate Specificity: Relative rates of ATP hydrolytic activity[a]

| Substrates | Relative rate |
|---|---|
| 50 ng linear DNA[b] | 1.000 |
| 1 µg circular DNA[c] | <0.002 |
| 1 µg t-RNA[d] | <0.002 |
| 1 µg MS2 RNA[e] | <0.002 |

[a]The coupled reaction (Methods) was used to evaluate the relative activities of the enzyme with various substrates. The enzymic activity approximated $V_{max}$ at 50 ng linear DNA, used in the assay.
[b]Linear DNA (HindIII digested Lambda DNA),
[c]Circular DNA (pUC4K),
[d]t-RNA of yeast (*S. cerevesiae*) origin, and the
[e]bacteriophage MS2 RNA (see Methods) were used as substrates and ADP formation was monitored.

TABLE 3

Effect of Inhibitors and Polynucleotides: Relative Rates of ATP Hydrolysis[a]

| | | |
|---|---|---|
| 50 | ng linear DNA | 1.000 |
| +10 | mM EDTA | 0.008 |
| +1 | mM citrate | 0.686 |
| 5 | ng linear DNA | 1.0 |
| +200 | ng t-RNA | 0.993 |
| +500 | ng circular DNA | 0.982 |
| +5% | ethanol | 0.86 |
| 10 | ng linear DNA | 1.99 |
| +200 | ng t-RNA | 1.996 |
| +500 | ng circular DNA | 1.994 |
| +5% | ethanol | 1.78 |
| 15 | ng linear DNA | 3.06 |
| +200 | ng t-RNA | 3.09 |
| +500 | ng circular DNA | 3.07 |
| +5% | ethanol | 2.64 |

[a]The effects of inhibitors and other polynucleotides were evaluated at sub-$K_m$ concentrations of the substrate to maximize their effects, using a coupled assay (Methods).

Example 2

Precise quantitation of linear DNA content may be determined using an ATP-dependent deoxyribonuclease. This method may be used to determine the linear DNA content of plasmid or restriction enzyme-digested plasmid DNA preparations, single stranded DNA preparations, gel isolated DNA fragments, PCR products and oligonucleotides. The spectrophotometric assay described herein can be used to quantify linear DNA at amounts as low as 2 ng in a reaction. The method not only allows determination of linear DNA in research samples, but also in plasmid preparations being evaluated for gene therapy and genetic vaccination.

Various concentrations of linearized DNA are provided as a substrate in an enzymatic reaction that uses ATP. ADP generated in the reaction is proportional to the cleavage of the phosphodiester bonds in DNA. At sub-$K_m$ concentrations of DNA (phosphodiester linkages), the enzymic reaction is proportional to substrate concentration (linear DNA). ADP formation is coupled to a detection module that consists of pyruvate kinase, phosphoenol pyruvate, lactate dehydrogenase, and NADH. Pyruvate kinase transfers the phosphoryl group of the phosphoenol pyruvate to ADP to form pyruvate and thus regenerates ATP. Pyruvate thus formed is converted to lactate by lactate dehydrogenase. This reaction utilizes NADH which is oxidized to NAD. Oxidation of NADH results in a loss of absorbance at 340 nm. Determination of the moles of NADH formed allows for the quantification of ADP formed in the reaction. Although NADH oxidation can be quantitated in real time by continuous spectrophotometric (microtiter plate) determinations at 340 nm, the detection is affected by DNA, nucleotides and protein molecules that absorb UV. By use of thio-NADH (TNADH) which absorbs at 405 nm, visible spectrophotometry is achieved, and thus its adaption to microtiter plate assay is easily achieved. The reaction is monitored in real time to determine initial velocity rates.

Assay preparation

Remove from cold storage the following items: ATP, PAP, DNAse enzyme, PK/LDH enzyme, 10× buffer, TNADH. Place items on ice. (Note: ATP, PEP and 10× buffer must completely thaw prior to running the assay.) Preparation of materials is as follows.

Solutions 1) 10× buffer. Prepare and autoclave the following stock solutions:
   1M Tris-Acetate, pH 7.8
   1M Potassium Acetate
   1M Magnesium Acetate
   DiH$_2$O
   Filter sterilized 1M DTT (made up with sterile water) and stored at −20° C.

Prepare 100 ml 10× buffer by mixing the appropriate amounts of the above solutions to achieve the following concentrations. Store 10× buffer at −20° C.

50 ml 1M Tris-Acetate, pH 7.8 at 25° C. 500 mM
25 ml 1M K-Acetate 250 mM
10 ml 1M Mg-Acetate 100 mM
5 ml DTT 50 mM
10 ml DiH$_2$O 2) Pyruvate Kinase/Lactate Dehydrogenate enzyme mix (from rabbit muscle) is from SIGMA Chemical Co. Catalog #PO294 (5 ml glycerol). The enzyme should be stored at −20° C. in a non-frost free freezer.

3) Thio-Nicotrinamaide Adenine Dinucleotide reduced (Thio-NADH) is from SIGMA Chemical Co. Catalog #PT4259. Thio-NADH in powder form is stored below 0° C. as suggested by SIGMA. However, the stock solution of 2 mg/ml (approximately 2.5 μmoles/ml) prepared in diH$_2$O is stored at 4° C. in a dark tube covered with aluminum foil as it is light sensitive. (The solution of Thio-NADH is good for at least one week but not linger than 10 days, when handled on ice or left at 4° C., and kept in the dark.) The stock solution is checked for concentration by serially diluting it ten fold at a time in water, and determining the absorbance at 405 nm. Thio-NADH when made up as described above (2 mg/ml) should have an absorbance at 400 nm of 20–30. (Concentration of solution is 2 mM calculated by absorbance at 400 nm×dilution factor divided by 10.3)

4) ATP-dependent exonuclease at 10 units/μL (Catalog #E3110K) is from Epicentre Technologies, Madison Wis. The enzyme solution is stored at −20° C. in a non-frost free freezer.

5) Phosphoenolpyruvate (PEP) Thio-NADH is from SIGMA Chemical Co. Catalog #P7002. A 76 mM (acceptable range is from 74–78 mM) solution is prepared in diH$_2$O, pH adjusted with 1N NaOH to 7.5, and is stored at −20° C. in a non-frost free freezer. (Use 1N acetic acid if acid is used to adjust the pH.) To estimate the concentration of PEP in the stock solution the following protocol is recommended. Ten fold serial dilutions of 1 ml are mode of the PEP stock solution. The 10× buffer previously described is used. The following reaction mix is prepared: 100 μL of 10× buffer, 40 μL of 25 mM ADP, 40 μL of PK/LDH enzyme mix, 120 μl thio-NADH (2 mg/ml) and 600 μl water. The concentration is spectrophotometrically determined at 400 nm. A blank reading is obtained by mixing 90 μL of the reaction mix with 10 μL of water (blank). In another tube 90 μL of reaction mix is combined with 10 μL of the serially diluted PEP stock solution nd is incubated for 5 minutes at 25° C. and its absorbance at 405 nm is noted (Exp). The PEP concentration in the stock solution in mM is determined using the following formula:

[(Blank)×(Exp)]×dilution factor×10 divided by 10.3.

A stock solution is thus prepared and 1 ml aliquots are made up and stored at −20° C. The solution is good for up to one year.

6) Adenosine triphosphate (ATP) is from SIGMA Chemical Co. Catalog #A7699. A 24 mM (acceptable range is from 22–25 mM) solution is prepared in diH$_2$O, pH adjusted with 1N NaOH to 7.5, and is stored at −20° C. in a non-frost free freezer. (Use 1N acetic acid if acid is used to adjust the pH.) The concentration of ATP is determined by making serial 10 fold dilutions in 1 ml, and determining its absorbance at 254 nm. The extinction coefficient of 15.2 absorbance at 254 nm for a 1 mM solution is used to calculate the concentration of ATP in the stock solution. To calculate the concentration of an ATP solution in 1 mM, the formula is: Absorbance of the diluted sample×the dilution factor divided by 15.2. A stock solution is thus prepared, and 1 ml aliquots are made and stored at −20° C. in a non-frost free freezer. The solution is good for up to one year.

7) The Diluent (make up volume): The assay procedure described within can accommodate 40 μL of the DNA sample. However, when using volumes of the standard and samples of less than 40 μL, assay diluent is used to make up volume.

Dilutions

Prepare samples, assay diluent and DNA standard curves according to the dilution schemes listed below.

1) Samples: When running samples of the first time it is unclear as to the amount of Linear DNA present in any given sample. Therefore, it may be necessary to run some samples more than one time in order to achieve a dilution which will produce results that fall within the linear range of the test. It may be advisable to run many different dilutions of the same sample the first time. In this manner, useable data may be obtained on the first plate.

2) Each sample dilution will be loaded in duplicate at 10, 20, 30 and 40 μL. All samples are to be diluted using the same buffer in which they are submitted. This same buffer, then, is also to be used as the Assay Diluent which will make up the volumes of each well to 40 uL.

3) Standards: A fresh dilution of a 1 ng/uL solution of Lambda DNA is prepared just prior to adding the standards. Calculate the proper dilution using the formula (X−1)=Y where 'X' is the total ng/μL of the lambda standard. Combine 1 μL of the lambda standard with 'Y' μL of the appropriate buffer. For example: the lambda standard is 575 ng/μL by HPLC, so the proper dilution is 1 μL standard+574 μL buffer.

4) The concentration of the stock Lambda DNA will change by lot number and should therefore be determined via HPLC in order to achieve a correct dilution of the standard. Submit new standards for HPLC concentration evaluation prior to running the test.

Template Preparation

1) The amount of sample DNA should be added to the wells, in duplicate, as follows: 10, 20, 30 and 40 μL, out of the total 40 μL to be added. The remaining volume is to be made up of Assay Diluent. The amount of Linear DNA in the samples will vary. If the mOD of the samples exceeds that of the Standard curve, higher dilutions are required. Be sure to include the Dilution Factor in the final calculations to achieve accurate Linear DNA counts.

Spike Recovery Set Up

On every plate run a spike recovery is carried out. If 3 dilutions of a sample are un on one plate, then a spike recovery curve must be set up for each dilution. A standard curve is generated in the buffer that the sample is in. The lambda DNA standard is loaded at 5, 10, 15 and 20 μL in duplicate. 10 μL of one sample dilution is added to each of the wells. The previously made up standard DNA and sample dilutions should be used in preparation of the spike recoveries.

Running the assay

1) Open the appropriate folder on the Spectramax plate reader, and set the temperature to 25° C.

2) Obtain a Corning flat bottomed 96 well Elisa plate. 3) A DNA standard curve consisting of 5, 10, 20, 30 and 40 μL in the appropriate buffer is to be run for each assay.

4) A spike recovery curve for each sample dilution consisting of 5, 10, 15 and 20 μL of standard DNA and 10 μL of sample dilution is to be run for each assay.

5) Load the appropriate amount of 10× Linear DNA Assay buffer (0.021 mL) into the designated Elisa plate wells.

6) Load the appropriate amount of Assay Diluent into the designated Elisa plate wells.

7) Load the appropriate amount of DNA samples into the designated Elisa plate wells.

8) Make the DNA standard dilution and load the appropriate amount the designated Elisa plate wells.

9) Prepare the reaction mixture as follows:
A) Count the number of wells that require reaction mixture.
B) Divide this number by 12 (volumes are based on 12 samples).
C) Add 0.6 to the resulting number and round up t the nearest tenth.
D) Multiply this number by the following given volumes for each reagent and combine in order:

0.3 mL TNADH
0.1 mL PK/LDH
0.1 mL ATP
0.038 mL PEP
1.192 mL DiH$_2$O
0.02 mL DNAse enzyme Mix gently, (do not vortex) and pour into a clean reservoir. Using a multi-channel pipette, add 146 μL of the reaction mixture to each well, including the DNA standard wells.

Calculating Amount of Linear DNA from the report

1) Each Linear DNA worksheet is designed for three dilutions of one sample, therefore, document each different sample on a separate worksheet.

2) Be sure the Standards are set to a linear curve. Data is in an acceptable range if the mOD reading of the samples lies within the mOD values of the Standard Curve. At least 3 of the 4 average mODs per dilution should fall within the standard values. (Ideally, the 20, 20 and 40 μL sample additions.) The Standard Curve must have a correlation coefficient of 0.980 or greater.

3) Take the average of the two values for the 40 μL standard. Take the average for the two 5 μL standard values. Subtract the 5 μL value from the 40 μL value and divide this number by 35 (The difference in μL of the two standards). The resulting number is the Standard Curve Value (STV).

4) Take the average of the two mOD readings for each sample.

5) Multiply that number by the Dilution Factor for that sample. (The dilution factor for each sample is attained by dividing the total amount of diluted sample made up by the amount of sample added to the dilution. For example, if 250 μL of a sample dilution was made and 50 μL of the sample was combined with 200 μL of Assay Diluent to make up that 250 uL, the Dilution Factor would be 250÷50=5.)

6) Take that number and divide it by the STV.

7) This resulting number is to be divided by the amount of μL of sample added to that well. This number is the amount, in ng/μL, of the Linear DNA in that sample. Do the same calculation for the 10, 20, 30 and 40 μL additions of sample, assuming all mODs fall within the linear range.

8) Take the average of the resulting numbers. This number, then, is to be divided by the total μg/μL of the known DNA in the original sample to attain the ng/μg Linear DNA in that sample.

Calculating Spike Recovery

1) Determine which of the sample dilutions yielded results that lie within the linear range of the assay.

2) Perform a linear regression on the spike recovery curve and a linear regression on the standard curve run with the assay. The difference in the slopes of the standard curves in the presence $(V_{SA})$ 100/$V_o$}.

3) The percentage recovery should fall between 80% to 120% to be considered as useable data.

Formulae

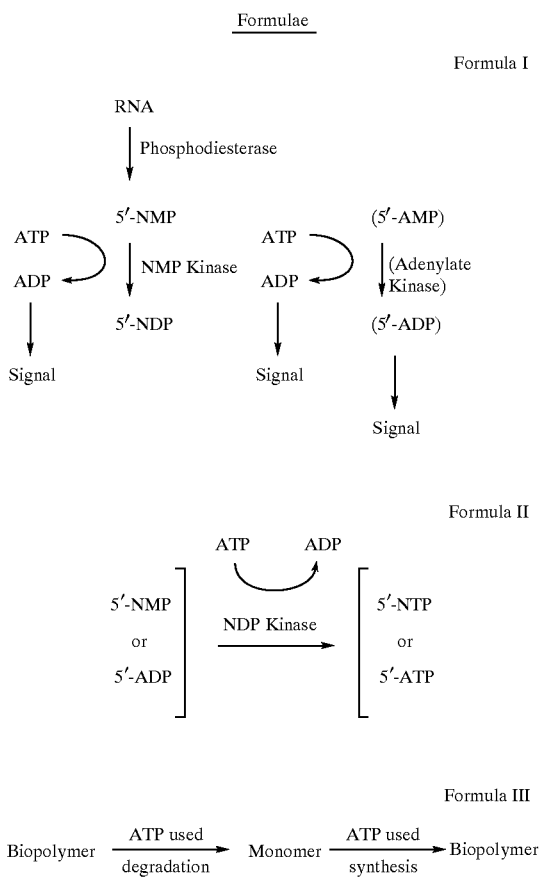

We claim:

1. A method of detecting the presence of linear double stranded DNA in a sample that contains circular DNA comprising the steps of:
   combining an ATP-dependent exodeoxyribonuclease, ATP and said sample to form a reaction mixture, wherein said ATP-dependent exodeoxyribonuclease is inactive in converting ATP to ADP in the absence of said linear double stranded DNA in said sample;
   maintaining said reaction mixture under conditions in which linear double stranded DNA is processed by said ATP-dependent exodeoxyribonuclease, and ATP is converted to ADP, wherein conversion of any of said ATP to ADP is due to processing of linear DNA by said ATP-dependent exodeoxyribonuclease;
   detecting the presence of ADP, wherein said presence of ADP is indicative of the presence of linear double stranded DNA.

2. The method of claim 1 wherein said ATP-dependent exodeoxyribonuclease is an ATP-dependent 5' exodeoxyribonuclease.

3. The method of claim 1 wherein said ATP-dependent exodeoxyribonuclease is an ATP-dependent 31' exodeoxyribonuclease.

4. The method of claim 1 wherein the ATP is gamma$^{32}$P-ATP and the presence of ADP is detected by using thin layer chromatography to separate gamma$^{32}$P-ATP, ADP and free $^{32}$P and detecting the presence of free $^{32}$P.

5. The method of claim 1 wherein the ATP is alpha$^{32}$P-ATP and the presence of ADP is detected by using thin layer chromatography to separate the alpha$^{32}$P-ATP, alpha$^{32}$P-ADP and free P, and detecting the presence of alpha$^{32}$P-ADP.

6. The method of claim 1 wherein the ATP is beta$^{32}$P-ATP and the presence of ADP is detected by using thin layer chromatography to separate the beta$^{32}$P-ATP, beta$^{32}$P-ADP and free P, and detecting the presence of beta$^{32}$P-ADP.

7. The method of claim 1 wherein the presence of ADP is detected by:
   further combining phosphoenolpyruvate, pyruvate kinase, lactate dehydrogenase, and NADH or TNADH, to said reaction mixture,
   maintaining the reaction mixture plus phosphoenolpyruvate, pyruvate kinase, lactate dehydrogenase and NADH or TNADH, under conditions wherein phosphoenolpyruvate in the presence of pyruvate kinase and ADP generated when said linear DNA is processed by said ATP-dependent exodeoxyribonuclease is phosphorylated is converted to pyruvate and said ADP is converted to ATP, wherein said pyruvate in the presence of said lactate dehydrogenase and NADH or TNADH forms lactate and NAD or TNAD,
   and measuring the amount of NADH or TNADH remaining, wherein if the amount of NADH or TNADH remaining is less than the amount of NADH or TNADH added to said reaction mixture, the presence of linear DNA is indicated.

8. The method of claim 7 wherein NADH is added to said reaction mixture, and the amount of NADH remaining is measured by spectrophotometry at 340 nm.

9. The method of claim 7 wherein TNADH is added to said reaction mixture, and the amount of TNADH remaining is measured by spectrophotometry at 405 nm.

10. The method of claim 7 further comprising the step of quantifying the number of linear DNA molecules present in said sample comprising the step of comparing the amount of NADH or TNADH remaining with data that show the amount of NADH or TNADH remaining from a series of control reactions that each use a different known number of linear DNA molecules as starting material.

11. A method of detecting the presence of DNA in a sample that contains circular DNA comprising the steps of:
    linearizing double stranded DNA in said sample by contacting said double stranded DNA with an endonuclease,
    combining an ATP-dependent exodeoxyribonuclease, ATP and said sample to form a reaction mixture, wherein said ATP-dependent exodeoxyribonuclease is inactive in converting ATP to ADP in the absence of said linear double stranded DNA in said sample;
    maintaining said reaction mixture under conditions in which linear double stranded DNA is processed by said ATP-dependent exodeoxyribonuclease, and ATP is converted to ADP, wherein conversion of any of said ATP to ADP is due to processing of linear DNA by said ATP-dependent exodeoxyribonuclease;
    detecting the presence of ADP, wherein said presence of ADP is indicative of the presence of DNA.

12. The method of claim 11 wherein said ATP-dependent deoxyribonuclease is selected form the group consisting of: ATP-dependent 5' exodeoxyribonuclease and ATP-dependent 3' exodeoxyribonuclease.

13. The method of claim 11 wherein said ATP-dependent deoxyribonuclease is selected form the group consisting of: ATP-dependent 5' exodeoxyribonuclease and ATP-dependent 3' exodeoxyribonuclease.

14. The method of claim 11 wherein the ATP is gamma$^{32}$P-ATP and the presence of ADP is detected by using thin layer chromatography to separate gamma$^{32}$P-ATP, ADP and free $^{32}$P and detecting the presence of free $^{32}$P.

15. The method of claim 11 wherein the ATP is alpha$^{32}$P-ATP and the presence of ADP is detected by using thin layer chromatography to separate the alpha$^{32}$P-ATP, alpha$^{32}$P-ADP and free P, and detecting the presence of alpha$^{32}$P-ADP.

16. The method of claim 11 wherein the ATP is beta$^{32}$P-ATP and the presence of ADP is detected by using thin layer chromatography to separate the beta$^{32}$P-ATP, beta$^{32}$P-ADP and free P, and detecting the presence of beta$^{32}$P-ADP.

17. The method of claim 11 wherein said sample comprises components selected from the group consisting of: viral particles, protein molecules, and microorganisms.

18. The method of claim 11 wherein the presence of ADP is detected by:
further combining phosphoenolpyruvate, pyruvate kinase, lactate dehydrogenase, and NADH or TNADH, to said reaction mixture,
maintaining the reaction mixture plus phosphoenolpyruvate, pyruvate kinase, lactate dehydrogenase and NADH or TNADH, under conditions wherein phosphoenolpyruvate in the presence of pyruvate kinase and ADP generated when said linear DNA is processed by said ATP-dependent deoxyribonuclease is phosphorylated is converted to pyruvate and said ADP is converted to ATP, wherein said pyruvate in the presence of said lactate dehydrogenase and NADH or TNADH forms lactate and NAD or TNAD,
and measuring the amount of NADH or TNADH remaining, wherein if the amount of NADH or TNADH remaining is less than the amount of NADH or TNADH added to said reaction mixture, the presence of DNA is indicated.

19. The method of claim 18 wherein NADH is added to said reaction mixture, and the amount of NADH remaining is measured by spectrophotometry at 340 nm.

20. The method of claim 18 wherein TNADH is added to said reaction mixture, and the amount of TNADH remaining is measured by spectrophotometry at 405 nm.

21. The method of claim 18 further comprising the step of quantifying the number of DNA molecules present in said sample comprising the step of comparing the amount of NADH or TNADH remaining with data that show the amount of NADH or TNADH remaining from a series of control reactions that each use a different known number of DNA molecules as starting material.

22. A method of detecting the presence of linear double stranded DNA in a sample that contains circular DNA comprising the steps of:
combining an ATP-dependent exodeoxyribonuclease, ATP and said sample to form a reaction mixture, wherein said ATP-dependent exodeoxyribonuclease is a *Micrococcus lysodeiklicus* ATP-dep endent exodeoxyribonuclease;
maintaining said reaction mixture under conditions in which linear double stranded DNA is processed by said ATP-dependent exodeoxyribonuclease, and ATP is converted to ADP;
detecting the presence of ADP, wherein said presence of ADP is indicative of the presence of linear double stranded DNA.

23. The method of claim 22 wherein the ATP is gamma$^{32}$P-ATP and the presence of ADP is detected by using thin layer chromatography to separate gamma$^{32}$P-ATP, ADP and free $^{32}$P and detecting the presence of free $^{32}$P.

24. The method of claim 22 wherein the ATP is alpha$^{32}$P-ATP and the presence of ADP is detected by using thin layer chromatography to separate the alpha$^{32}$P-ATP, alpha$^{32}$P-ADP and free P, and detecting the presence of alpha$^{32}$P-ADP.

25. The method of claim 22 wherein the ATP is beta3$^{2}$P-ATP and the presence of ADP is detected by using thin layer chromatography to separate the beta$^{32}$P-ATP, beta$^{32}$P-ADP and free P, and detecting the presence of beta$^{32}$P-ADP.

26. The method of claim 22 wherein the presence of ADP is detected by:
further combining phosphoenolpyruvate, pyruvate kinase, lactate dehydrogenase, and NADH or TNADH, to said reaction mixture,
maintaining the reaction mixture plus phosphoenolpyruvate, pyruvate kinase, lactate dehydrogenase and NADH or TNADH, under conditions wherein phosphoenolpyruvate in the presence of pyruvate kinase and ADP generated when said linear DNA is processed by said ATP-dependent exodeoxyribonuclease is phosphorylated is converted to pyruvate and said ADP is converted to ATP, wherein said pyruvate in the presence of said lactate dehydrogenase and NADH or TNADH forms lactate and NAD or TNAD,
and measuring the amount of NADH or TNADH remaining, wherein if the amount of NADH or TNADH remaining is less than the amount of NADH or TNADH added to said reaction mixture, the presence of linear DNA is indicated.

27. The method of claim 26 wherein NADH is added to said reaction mixture, and the amount of NADH remaining is measured by spectrophotometry at 340 nm.

28. The method of claim 26 wherein TNADH is added to said reaction mixture, and the amount of TNADH remaining is measured by spectrophotometry at 405 nm.

29. The method of claim 26 further comprising the step of quantifying the number of linear DNA molecules present in said sample comprising the step of comparing the amount of NADH or TNADH remaining with data that show the amount of NADH or TNADH remaining from a series of control reactions that each use a different known number of linear DNA molecules as starting material.

30. A method of detecting the presence of DNA in a sample that contains circular DNA comprising the steps of:
linearizing double stranded DNA in said sample by contacting said double stranded DNA with an endonuclease,
combining an ATP-dependent exodeoxyribonuclease, ATP and said sample to form a reaction mixture, wherein said ATP-dependent exodeoxyribonuclease is a *Micrococcus lysodeiklicus* ATP-dependent exodeoxyribonuclease;
maintaining said reaction mixture under conditions in which linear double stranded DNA is processed by said ATP-dependent exodeoxyribonuclease, and ATP is converted to ADP;
detecting the presence of ADP, wherein said presence of ADP is indicative of the presence of DNA.

31. The method of claim 30 wherein the ATP is gamma$^{32}$P-ATP and the presence of ADP is detected by using thin layer chromatography to separate gamma$^{32}$P-ATP, ADP and free $^{32}$P and detecting the presence of free $^{32}$P.

32. The method of claim 30 wherein the ATP is alpha$^{32}$P-ATP and the presence of ADP is detected by using thin layer chromatography to separate the alpha$^{32}$P-ATP, alpha$^{32}$P-ADP and free P, and detecting the presence of alpha$^{32}$P-ADP.

33. The method of claim 30 wherein the ATP is beta$^{32}$P-ATP and the presence of ADP is detected by using thin layer chromatography to separate the beta$^{32}$P-ATP, beta$^{32}$P-ADP and free P, and detecting the presence of beta$^{32}$P-ADP.

34. The method of claim 30 wherein said sample comprises components selected from the group consisting of: viral particles, protein molecules, and microorganisms.

35. The method of claim 30 wherein the presence of ADP is detected by:

further combining phosphoenolpyruvate, pyruvate kinase, lactate dehydrogenase, and NADH or TNADH, to said reaction mixture, maintaining the reaction mixture plus phosphoenolpyruvate, pyruvate kinase, lactate dehydrogenase and NADH or TNADH, under conditions wherein phosphoenolpyruvate in the presence of pyruvate kinase and ADP generated when said linear DNA is processed by said ATP-dependent deoxyribonuclease is phosphorylated is converted to pyruvate and said ADP is converted to ATP, wherein said pyruvate in the presence of said lactate dehydrogenase and NADH or TNADH forms lactate and NAD or TNAD, and measuring the amount of NADH or TNADH remaining, wherein if the amount of NADH or TNADH remaining is less than the amount of NADH or TNADH added to said reaction mixture, the presence of DNA is indicated.

36. The method of claim 35 wherein NADH is added to said reaction mixture, and the amount of NADH remaining is measured by spectrophotometry at 340 nm.

37. The method of claim 35 wherein TNADH is added to said reaction mixture, and the amount of TNADH remaining is measured by spectrophotometry at 405 nm.

38. The method of claim 35 further comprising the step of quantifying the number of DNA molecules present in said sample comprising the step of comparing the amount of NADH or TNADH remaining with data that show the amount of NADH or TNADH remaining from a series of control reactions that each use a different known number of DNA molecules as starting material.

* * * * *